(12) United States Patent
Root et al.

(10) Patent No.: US 10,009,407 B2
(45) Date of Patent: *Jun. 26, 2018

(54) ANALYTE DATA RETRIEVER

(71) Applicant: DexCom, Inc., San Diego, CA (US)

(72) Inventors: Daniel N. Root, Portland, OR (US); Justin E. Schumacher, Portland, OR (US); Adam R. Greene, Portland, OR (US); Stewart Alan Shields, Beaverton, OR (US)

(73) Assignee: DexCom, Inc., San Diego, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/642,729

(22) Filed: Jul. 6, 2017

(65) Prior Publication Data

US 2017/0310733 A1 Oct. 26, 2017

Related U.S. Application Data

(63) Continuation of application No. 13/734,639, filed on Jan. 4, 2013, now Pat. No. 9,736,210, which is a
(Continued)

(51) Int. Cl.
*G06F 7/04* (2006.01)
*G06F 17/30* (2006.01)
(Continued)

(52) U.S. Cl.
CPC .............. *H04L 67/02* (2013.01); *G06F 19/30* (2013.01); *G06F 19/3418* (2013.01);
(Continued)

(58) Field of Classification Search
None
See application file for complete search history.

(56) References Cited

U.S. PATENT DOCUMENTS

| 8,401,194 | B2 * | 3/2013 | Nierzwick | ............ | H04L 63/061 |
| | | | | | 380/270 |
| 9,618,967 | B2 * | 4/2017 | Brown | .................. | G06F 1/1605 |
| 9,715,327 | B2 * | 7/2017 | Rosinko | ................ | G06F 3/0484 |
| 2005/0038680 | A1 * | 2/2005 | McMahon | ........... | A61B 5/0022 |
| | | | | | 705/3 |

(Continued)

FOREIGN PATENT DOCUMENTS

WO  WO-2011091336 A1 *  7/2011  ............... A61B 5/01

*Primary Examiner* — Farid Homayounmehr
*Assistant Examiner* — Olanrewaju J Bucknor
(74) *Attorney, Agent, or Firm* — Knobbe Martens Olson & Bear, LLP

(57) ABSTRACT

Methods and apparatus, including computer program products, are provided for processing analyte data. In some example implementations, a method may include receiving, at a first processing system including a user interface, an installation package including a plug-in and code configured to provide at the first processing system an interface between a sensor system configured to measure an analyte concentration level in a host and a second processing system; storing, by the first processing system, the installation package in a location based on a role of a user initiating the installation of the code; installing the plug-in for the user interface to enable the plug-in to control one or more aspects of an installation of the code; and initiating, by at least the plug-in, the installation of the code at the first processing system to provide the interface. Related systems, methods, and articles of manufacture are also disclosed.

14 Claims, 14 Drawing Sheets

Related U.S. Application Data continuation of application No. 13/734,423, filed on Jan. 4, 2013, now Pat. No. 8,844,057.

(60) Provisional application No. 61/708,464, filed on Oct. 1, 2012.

(51) Int. Cl.
*H04L 29/08* (2006.01)
*G06F 21/62* (2013.01)
*G06F 19/00* (2018.01)
*G16H 40/40* (2018.01)
*G16H 50/20* (2018.01)
*H04L 29/06* (2006.01)

(52) U.S. Cl.
CPC ......... *G06F 21/6245* (2013.01); *G16H 40/40* (2018.01); *G16H 50/20* (2018.01); *H04L 67/12* (2013.01); *H04L 63/0428* (2013.01); *H04L 63/18* (2013.01)

(56) References Cited

U.S. PATENT DOCUMENTS

| | | | | |
|---|---|---|---|---|
| 2008/0103447 A1* | 5/2008 | Reggiardo | ........ | A61M 5/14244 604/131 |
| 2010/0222648 A1* | 9/2010 | Tan | ..................... | G06F 19/3412 600/301 |
| 2010/0274218 A1* | 10/2010 | Yodfat | ................ | A61M 5/1413 604/504 |
| 2011/0210951 A1* | 9/2011 | Guthrie | ................ | G09G 3/3611 345/204 |

* cited by examiner

ANALYTE DATA RETRIEVER

INCORPORATION BY REFERENCE TO RELATED APPLICATION

Any and all priority claims identified in the Application Data Sheet, or any correction thereto, are hereby incorporated by reference under 37 CFR 1.57. This application is a continuation of U.S. application Ser. No. 13/734,639, filed Jan. 4, 2013, which is a continuation of U.S. application Ser. No. 13/734,423, filed Jan. 4, 2013, now U.S. Pat. No. 8,844,057, which claims the benefit of U.S. Provisional Application No. 61/708,464 filed Oct. 1, 2012, each of which is incorporated by reference herein in its entirety, and each of which is hereby made a part of this specification.

FIELD

The present disclosure generally relates to data processing of analyte data of a host.

BACKGROUND

Diabetes mellitus is a disorder in which the pancreas cannot create sufficient insulin, such as in the case of Type I diabetes and/or in which insulin is not effective, such as Type 2 diabetes. In a diabetic state, a victim suffers from high blood sugar, which causes an array of physiological derangements, such as kidney failure, skin ulcers, or bleeding into the vitreous of the eye, associated with the deterioration of small blood vessels. A hypoglycemic reaction, such as low blood sugar, may be induced by an inadvertent overdose of insulin, or after a normal dose of insulin or glucose-lowering agent accompanied by extraordinary exercise or insufficient food intake.

A diabetic person may carry a self-monitoring blood glucose (SMBG) monitor, which typically requires uncomfortable finger pricking methods. Due to the lack of comfort and convenience, a diabetic typically measures his or her glucose level only two to four times per day. Unfortunately, these time intervals are spread so far apart that the diabetic will likely find out too late, sometimes incurring dangerous side effects, of a hyperglycemic or hypoglycemic condition. In fact, it is not only unlikely that a diabetic will take a timely SMBG value, but additionally the diabetic will not know if his blood glucose value is higher or lower based on conventional methods.

Consequently, a variety of non-invasive, transdermal (e.g., transcutaneous) and/or implantable electrochemical sensors are being developed for continuously detecting and/or quantifying blood glucose values. These devices and other types of devices generally transmit raw or minimally processed data for subsequent analysis at a remote device, which can include a display, to allow presentation of information to a user hosting the sensor.

SUMMARY

In a first aspect, a method is provided comprising: receiving, at a first processing system comprising a user interface, an installation package comprising a plug-in and code configured to provide at the first processing system an interface between a sensor system configured to measure an analyte concentration level in a host and a second processing system; storing, by the first processing system, the installation package in a location based on a role of a user initiating installation of the code; installing the plug-in for the user interface to enable the plug-in to control one or more aspects of the installation of the code; initiating, by at least the plug-in, the installation of the code at the first processing system to provide the user interface; and forwarding, by the user interface at the first processing system, analyte sensor data to the second processing system.

In an embodiment of the first aspect, the first processing system further comprises a display for presenting the analyte sensor data, and wherein the first processing system couples to the sensor system via a first encrypted connection and further couples through a second encrypted connection to the second processing system, wherein the second processing system authorizes the first encrypted connection and the second encrypted connection.

In an embodiment of the first aspect, the second processing system further comprises a receiver configured to receive analyte sensor data and a processor configured to process the analyte sensor data forwarded by the interface, provide the plug-in to the first processing system, to provide the code to the first processing system, and to provide authorization and authentication of the user.

In an embodiment of the first aspect, the second processing system further comprises a repository configured to store a plurality of analyte sensor data for a plurality of users, wherein the stored analyte sensor data is encrypted to maintain privacy between each of the plurality of users accessing the second processing system including the repository through the internet.

In an embodiment of the first aspect, the storing further comprises: storing the code in the location accessible by a plurality of users of an organization, when the role of the user initiating the installation of the code corresponds to an administrator.

In an embodiment of the first aspect, the method further comprises storing the code in another location with access limited to an initiator of the installation of the code, when the role does not correspond to the administrator.

In an embodiment of the first aspect, the method further comprises obtaining, by the plug-in, a version of the code being used at the first processing system to provide the interface.

In an embodiment of the first aspect, the method further comprises comparing, by the plug-in, the obtained version with another version for the interface available at the first system to enable a determination of whether to update the code for the interface.

In an embodiment of the first aspect, the host is the user.

In an embodiment of the first aspect, the plug-in comprises a user interface plug-in.

In an embodiment of the first aspect, the plug-in comprises a plug-in to an internet browser software application.

In an embodiment of the first aspect, a processor of the first processing system performs the operations of the method by executing code embodied in a non-transitory computer-readable medium.

In a second aspect, an apparatus is provided comprising: at least one processor; and at least one memory including code which when executed by the at least one processor provides operations comprising: receiving, at a first processing system including a user interface, an installation package including a plug-in and code configured to provide at the first processing system an interface between a sensor system configured to measure an analyte concentration level in a host and a second processing system; storing, by the first processing system, the installation package in a location based on a role of a user initiating the installation of the code; installing the plug-in for the user interface to enable the plug-in to control one or more aspects of the installation of the code; initiating, by at least the plug-in, the installation of the code at the first processing system to provide the user interface; and forwarding, by the interface at the first processing system, analyte sensor data to the second processing system.

In an embodiment of the second aspect, the first processing system further comprises a display for presenting the analyte sensor data, and wherein the first processing system is configured to couple to the sensor system via a first encrypted connection and is further configured to couple through a second encrypted connection to the second processing system, wherein the second processing system authorizes the first encrypted connection and the second encrypted connection.

In an embodiment of the second aspect, the second processing system further comprises a receiver configured to receive analyte sensor data and a processor configured to process the analyte sensor data forwarded by the interface, to provide the plug-in to the first processing system, to provide the code to the first processing system, and to provide authorization and authentication of the user.

In an embodiment of the second aspect, the second processing system further comprises a repository configured to store a plurality of analyte sensor data for a plurality of users, wherein the stored analyte sensor data is encrypted to maintain privacy between each of the plurality of users accessing the second processing system including the repository through the internet.

In an embodiment of the second aspect, the storing further comprises: storing the code in the location accessible by a plurality of users of an organization, when the role of the user initiating the installation of the code corresponds to an administrator.

In an embodiment of the second aspect, the apparatus is further configured to store the code in another location with access limited to an initiator of the installation of the code, when the role does not correspond to the administrator.

In an embodiment of the second aspect, the apparatus is further configured to obtain, by the plug-in, a version of the code being used at the first processing system to provide the interface.

In an embodiment of the second aspect, the apparatus is further configured to compare, by the plug-in, the obtained version with another version for the interface available at the first system to enable a determination of whether to update the code for the interface.

In an embodiment of the second aspect, the host is the user.

In an embodiment of the second aspect, the plug-in comprises a user interface plug-in.

In a third aspect, a method is provided comprising: retrieving, using a first processing system comprising an interface, analyte sensor data from an analyte sensor system configured to measure an analyte concentration level in a host; and forwarding, by the interface, the received analyte sensor data as a pass-through by at least forwarding the received analyte sensor data to a second processing system coupled to the interface via a network including an internet, wherein the pass-through comprises forwarding the received analyte sensor data without storing the received analyte sensor data in a persistent storage at the first processing system comprising the interface.

In an embodiment of the third aspect, the first processing system further comprises a display for presenting the analyte sensor data, and wherein the first processing system couples to the sensor system via a first encrypted connection and further couples through a second encrypted connection to the second processing system, wherein the second processing system authorizes the first encrypted connection and the second encrypted connection.

In an embodiment of the third aspect, the interface comprises a data retriever software application that comprises a plug-in to an internet browser software application.

In an embodiment of the third aspect, the method further comprises storing the retrieved analyst sensor in memory of the second processing system, the second processing system comprising a server.

In an embodiment of the third aspect, the method further comprises detecting a connection of the analyte sensor system with the first processing system and automatically initiating a data retrieval application incorporated in the first processing system responsive to the detection, the data retrieval application performing the retrieving and the forwarding.

In an embodiment of the third aspect, the data retrieval application programmatically prompts a user on a user interface of the first processing system to initiate the retrieving and the forwarding, and wherein the retrieving and forwarding are initiated when the user selects the prompt.

In an embodiment of the third aspect, the data retrieval application programmatically initiates the retrieving and the forwarding without user interaction.

In a fourth aspect, an apparatus is provided comprising: at least one processor; and at least one memory including code which when executed by the at least one processor provides operations comprising: retrieving, using a first processing system comprising an interface, analyte sensor data from an analyte sensor system configured to measure an analyte concentration level in a host; and forwarding, by the interface, the received analyte sensor data as a pass-through by at least forwarding the received analyte sensor data to a second processing system coupled to the interface via a network including an internet, wherein the pass-through comprises forwarding the received analyte sensor data without storing the received analyte sensor data in a persistent storage at the first processing system including the interface.

In an embodiment of the fourth aspect, the first processing system further comprises a display configured for presenting the analyte sensor data, and wherein the first processing system is configured to couple to the sensor system via a first encrypted connection and is further configured to couple through a second encrypted connection to the second processing system, wherein the second processing system authorizes the first encrypted connection and the second encrypted connection.

In an embodiment of the fourth aspect, the code comprises an internet browser application and a plug-in to the internet browser software application that configures the internet browser application to performing the retrieving and the forwarding.

In an embodiment of the fourth aspect, the operations further comprise storing the retrieving analyst sensor in memory of the second processing system, and wherein the second processing system comprises a server.

In an embodiment of the fourth aspect, the operations further comprise detecting a connection of the analyte sensor system with the first processing system and automatically initiating the retrieving and the forwarding.

In an embodiment of the fourth aspect, the operations further comprise programmatically prompting a user on a user interface of the first processing system to initiate the retrieving and the forwarding upon detecting a connection of the analyte sensor system with the first processing system, and wherein the retrieving and forwarding are initiated when the user selects the prompt.

In a fifth aspect, a method is provided comprising inhibiting access to analyte sensor data measuring an analyte concentration level in a host, when a command is received to place in a blind mode one or more of an interface and a sensor system configured to measure the analyte concentration level in the host; and forwarding the analyte sensor data to an analyte processing system, wherein the access to the analyte sensor data is inhibited by at least preventing a display of the analyte sensor data at one or more of the interface and the sensor system.

In an embodiment of the fifth aspect, the interface comprises a processor and a display for displaying the analyte sensor data, and wherein the interface couples to the sensor system via a first encrypted connection and further couples through a second encrypted connection to the analyte processing system.

In an embodiment of the fifth aspect, the method further comprises receiving, from the analyte processing system, the command to place in the blind mode at least one of the interface and the sensor system.

In an embodiment of the fifth aspect, the method further comprises accessing a remote processing system using the interface, the remote processing system having computer instructions configured to cause the inhibiting.

In an embodiment of the fifth aspect, the interface comprises an internet browser and a browser plug-in, the plug-in configured to cause the internet browser to access the remote processing system and communicate with the sensor system.

In an embodiment of the fifth aspect, the method further comprises registering the sensor system for a particular use, the registering comprising associating the sensor system with a file pertaining the particular use.

In an embodiment of the fifth aspect, the registering further comprises one or more of clearing data from persistent memory of the sensor system, setting a clock of the sensor system or placing the sensor system in the blind or an unblind mode.

In an embodiment of the fifth aspect, the inhibiting is performed when the sensor system is set to the blind mode, and wherein the inhibiting is not performed when the sensor is in the unblind mode.

In an embodiment of the fifth aspect, the registering is performed programmatically responsive to a user selection of a prompt on the interface.

In a sixth aspect, an apparatus is provided comprising: at least one processor; and at least one memory including code which when executed by the at least one processor provides operations comprising: inhibiting access to analyte sensor data measuring an analyte concentration level in a host, when a command is received to place in a blind mode one or more of an interface and a sensor system configured to measure the analyte concentration level in the host; and forwarding the analyte sensor data to an analyte processing system, wherein the access to the analyte sensor data is inhibited by at least preventing a display of the analyte sensor data at one or more of the interface and the sensor system.

In an embodiment of the sixth aspect, the interface comprises a processor and a display for displaying the analyte sensor data, and wherein the interface is configured to couple to the sensor system via a first encrypted connection and is further configured to couple through a second encrypted connection to the analyte processing system.

In an embodiment of the sixth aspect, the apparatus is further configured to receive, from the analyte processing system, the command to place in the blind mode at least one of the interface and the sensor system.

In an embodiment of the sixth aspect, the operations further comprise accessing a remote processing system using the interface, the remote processing system having computer instructions configured to cause the inhibiting.

In an embodiment of the sixth aspect, the interface comprises an internet browser and a browser plug-in, the plug-in configured to cause the internet browser to access the remote processing system and communicate with the sensor system.

In an embodiment of the sixth aspect, the operations further comprise registering the sensor system for a particular use, the registering comprising associating the sensor system with a file pertaining the particular use.

In an embodiment of the sixth aspect, the registering further comprises one or more of clearing data from persistent memory of the sensor system, setting a clock of the sensor system or placing the sensor system in the blind or an unblind mode.

In an embodiment of the sixth aspect, the inhibiting is performed when the sensor system is set to the blind mode, and wherein the inhibiting is not performed when the sensor is in the unblind mode.

In an embodiment of the sixth aspect, the registering is performed programmatically responsive to a user selection of a prompt on the interface.

In addition to the above, methods and apparatus, including computer program products, are provided for data processing of analyte data. In some exemplary implementations, there is provided a method. The method may include receiving, at a first processing system including a user interface, an installation package including a plug-in and code configured to provide at the first processing system an interface between a sensor system configured to measure an analyte concentration level in a host and a second processing system; storing, by the first processing system, the installation package in a location based on a role of a user initiating the installation of the code; installing the plug-in for the user interface to enable the plug-in to control one or more aspects of an installation of the code; initiating, by at least the plug-in, the installation of the code at the first processing system to provide the interface; and forwarding, by the interface at the first processing system, analyte sensor data to the second processing system.

In another aspect, there is provided a system including at least one processor and at least one memory including code which when executed by the at least one processor causes operations comprising: receiving, at a first processing system including a user interface, an installation package including a plug-in and code configured to provide at the first processing system an interface between a sensor system configured to measure an analyte concentration level in a host and a second processing system; storing, by the first processing system, the installation package in a location based on a role of a user initiating the installation of the code; installing the plug-in for the user interface to enable the plug-in to control one or more aspects of an installation of the code; initiating, by at least the plug-in, the installation of the code at the first processing system to provide the interface; and forwarding, by the interface at the first processing system, analyte sensor data to the second processing system.

In yet another aspect, there is provided a computer-readable storage medium including code which when executed by the at least one processor causes operations comprising: receiving, at a first processing system including a user interface, an installation package including a plug-in and code configured to provide at the first processing system an interface between a sensor system configured to measure an analyte concentration level in a host and a second processing system; storing, by the first processing system, the installation package in a location based on a role of a user initiating the installation of the code; installing the plug-in for the user interface to enable the plug-in to control one or more aspects of an installation of the code; initiating, by at least the plug-in, the installation of the code at the first processing system to provide the interface; and forwarding, by the interface at the first processing system, analyte sensor data to the second processing system.

In some implementations, the above-noted aspects may further include additional features described herein including one or more of the following. The first processing system may further comprise a display for presenting the analyte sensor data, and wherein the first processing system may couple to the sensor system via a first encrypted connection and may further couple through a second encrypted connection to the second processing system. The second processing system may authorize the first encrypted connection and the second encrypted connection. The second processing system may further comprise a receiver configured to receive analyte sensor data and a processor configured to process the analyte sensor data forwarded by the interface, provide the plug-in to the first processing system, provide the code to the first processing system, and provide authorization and authentication of the user. The second processing system may further comprise a repository configured to store a plurality of analyte sensor data for a plurality of users, wherein the stored analyte sensor data is encrypted to maintain privacy between each of the plurality of users accessing the second processing system including the repository through the Internet. The storing may further comprise storing the code in the location accessible by a plurality of users of an organization, when the role of the user initiating the installation of the code corresponds to an administrator. The code may be stored in another location with access limited to an initiator of the installation of the code, when the role does not correspond to the administrator. The plug-in may obtain a version of the code being used at the first processing system to provide the interface. The plug-in may also compare obtained version with another version for the interface available at the first system to enable a determination of whether to update the code for the interface. The host may comprise the user. The plug-in may comprise a user interface plug-in.

In yet another aspect, there is provided a method. The method may include receiving, at first processing system including an interface, analyte sensor data from an analyte sensor system configured to measure an analyte concentration level in a host; and forwarding, by the interface, the received analyte sensor data as a pass-through by at least forwarding the received analyte sensor data to a second processing system coupled to the interface via a network including an Internet, wherein the pass-through comprises forwarding the received analyte sensor data without storing the received analyte sensor data in a persistent storage at the first processing system including the interface. While in other aspects, systems, apparatus, and computer-readable storage media may also be provided.

In some implementations, the above-noted aspects may further include additional features described herein including one or more of the following. The first processing system may further comprise a display for presenting the analyte sensor data, and wherein the first processing system may couple to the sensor system via a first encrypted connection and may further couple through a second encrypted connection to the second processing system, wherein the second processing system authorizes the first encrypted connection and the second encrypted connection.

In another aspect, there is provided a method. The method may include inhibiting access to analyte sensor data measuring an analyte concentration level in a host, when a command is received to place in a blind mode one or more of an interface and a sensor system configured to measure the analyte concentration level in the host; and forwarding the analyte sensor data to an analyte processing system, wherein the access to the analyte sensor data is inhibited by at least preventing a display of the analyte sensor data at one or more of the interface and the sensor system. While in other aspects, systems, apparatus, and computer-readable storage media may also be provided.

In some implementations, the above-noted aspects may further include additional features described herein including one or more of the following. The interface may include a processor and a display for displaying the analyte sensor data, and wherein the interface may couple to the sensor system via a first encrypted connection and may further couple through a second encrypted connection to the analyte processing system. The command may be received from the analyte processing system to place in the blind mode one or more of the interface and the sensor system.

It is to be understood that both the foregoing general description and the following detailed description are exemplary and explanatory only and are not restrictive. Further features and/or variations may be provided in addition to those set forth herein. For example, the implementations described herein may be directed to various combinations and subcombinations of the disclosed features and/or combinations and subcombinations of several further features disclosed below in the detailed description.

Figure 1:
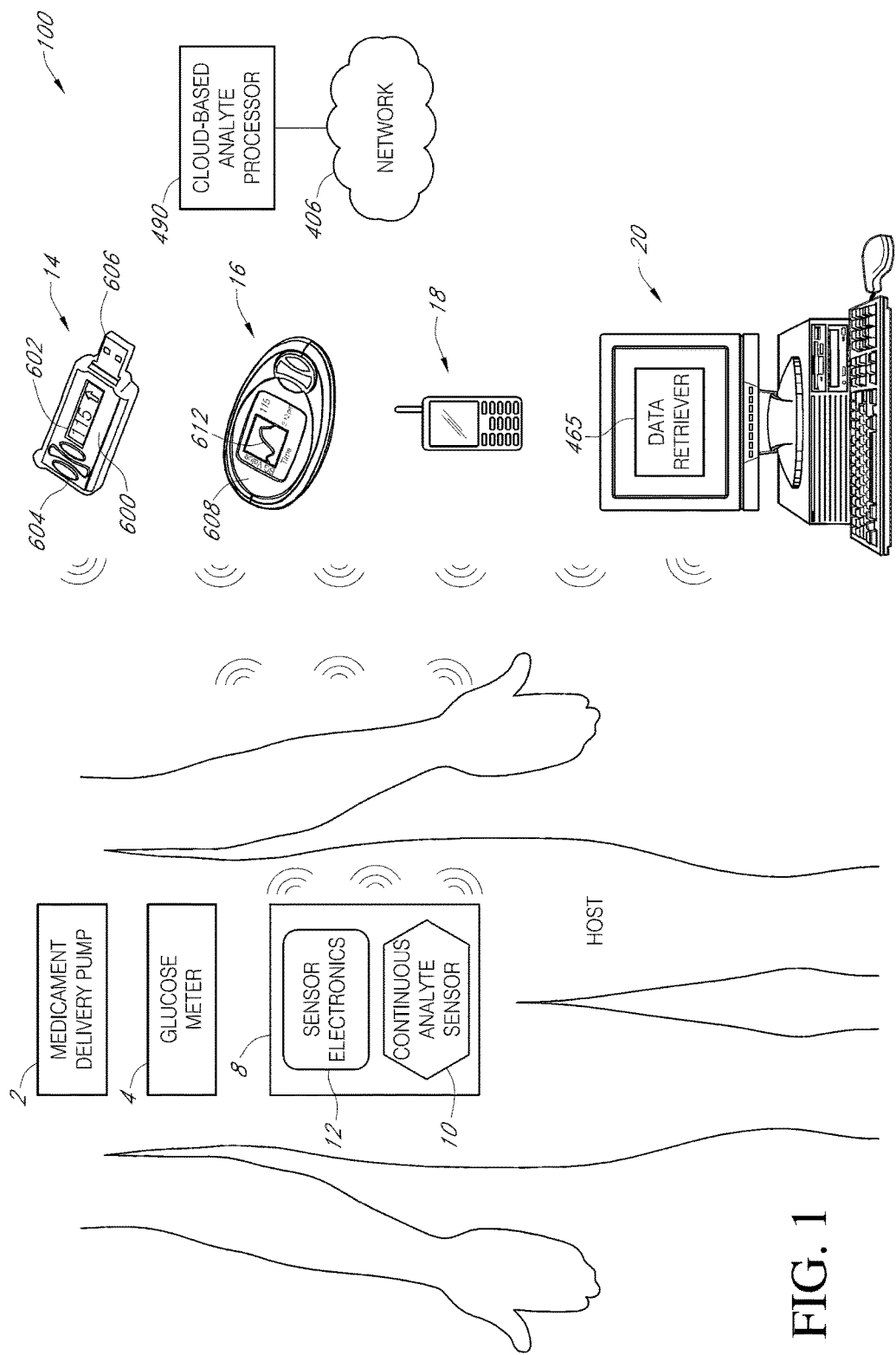
FIG. 1 depicts a diagram illustrating a continuous analyte sensor system including a sensor electronics module in accordance with some exemplary implementations.

Like labels are used to refer to same or similar items in the drawings.

DETAILED DESCRIPTION

FIG. 1 depicts an example system 100, in accordance with some exemplary implementations. The system 100 includes a continuous analyte sensor system 8 including a sensor electronics module 12 and a continuous analyte sensor 10. The system 100 may include other devices and/or sensors, such as medicament delivery pump 2 and glucose meter 4. The continuous analyte sensor 10 may be physically connected to sensor electronics module 12 and may be integral with (e.g., non-releasably attached to) or releasably attachable to the continuous analyte sensor 10. The sensor electronics module 12, medicament delivery pump 2, and/or glucose meter 4 may couple with one or more devices, such as display devices 14, 16, 18, and/or 20.

In some exemplary implementations, the system 100 may include a cloud-based analyte processor 490 configured to analyze analyte data (and/or other patient related data) provided via network 406 (e.g., via wired, wireless, or a combination thereof) from sensor system 8 and other devices, such as display devices 14-20 and the like, associated with the host (also referred to as a patient) and generate reports providing high-level information, such as statistics, regarding the measured analyte over a certain time frame. Although the example implementation described with respect to FIG. 1 refers to analyte data being received by analyte processor 490, other types of data processed and raw data may be received as well.

The system 100 may also include a data retriever 465 interfacing devices providing data, such as sensor system 8 and the like, and analyte processor 490. In some implementations, the data retriever 465 may interface a sensor system, receive sensor data from the sensor system, and forward the sensor data to analyte processor 490. Moreover, the forwarding may be performed as a pass-through, such that the sensor data is not stored in a persistent storage device at data retriever 465 (although the data may be buffered at the data retriever in transient memory (e.g., volatile memory) to support transmission) but instead forwarded directly to analyte processor 490. In addition, data retriever 465 may also be installed programmatically on a processor, such as computer 20, and may be updated programmatically as well. In some implementations, the data retriever comprises a plug-in software application to a commercially available Internet browsing software application, such as Microsoft Internet Explorer available from Microsoft, Inc., Firefox available from Mozilla Corporation, and Safari available from Apple, Inc. Furthermore, data retriever 465 and/or sensor system 8 may be commanded into a so-called "blind mode," such that sensor data generated by sensor system 8 cannot be viewed by the user wearing, or coupled to, the sensor system 8. Before describing additional features of data retriever 465, the following provides a description of the sensors and sensor systems that may be used in conjunction with data retriever 465.

In some exemplary implementations, the sensor electronics module 12 may include electronic circuitry associated with measuring and processing data generated by the continuous analyte sensor 10. This generated continuous analyte sensor data may also include algorithms, which can be used to process and calibrate the continuous analyte sensor data, although these algorithms may be provided in other ways as well. The sensor electronics module 12 may include hardware, firmware, software, or a combination thereof to provide measurement of levels of the analyte via a continuous analyte sensor, such as a continuous glucose sensor. An example implementation of the sensor electronics module 12 is described further below with respect to FIG. 2.

The sensor electronics module 12 may, as noted, couple (e.g., wirelessly and the like) with one or more devices, such as display devices 14, 16, 18, and/or 20. The display devices 14, 16, 18, and/or 20 may be configured for presenting (and/or alarming) information, such as sensor information transmitted by the sensor electronics module 12 for display at the display devices 14, 16, 18, and/or 20.

The display devices may include a relatively small, key fob-like display device 14, a relatively large, hand-held display device 16, a cellular phone (e.g., a smart phone, a tablet, and the like), a computer 20, and/or any other user equipment configured to at least present information (e.g., a medicament delivery information, discrete self-monitoring glucose readings, heart rate monitor, caloric intake monitor, and the like).

In some exemplary implementations, the relatively small, key fob-like display device 14 may comprise a wrist watch, a belt, a necklace, a pendent, a piece of jewelry, an adhesive patch, a pager, a key fob, a plastic card (e.g., credit card), an identification (ID) card, and/or the like. This small display device 14 may include a relatively small display (e.g., smaller than the large display device) and may be configured to display certain types of displayable sensor information, such as a numerical value and an arrow.

In some exemplary implementations, the relatively large, hand-held display device 16 may comprise a hand-held receiver device, a palm-top computer, and/or the like. This large display device may include a relatively larger display (e.g., larger than the small display device) and may be configured to display information, such as a graphical representation of the continuous sensor data including current and historic sensor data output by sensor system 8.

In some exemplary implementations, the continuous analyte sensor 10 comprises a sensor for detecting and/or measuring analytes, and the continuous analyte sensor 10 may be configured to continuously detect and/or measure analytes as a non-invasive device, a subcutaneous device, a transdermal device, and/or an intravascular device. In some exemplary implementations, the continuous analyte sensor 10 may analyze a plurality of intermittent blood samples, although other analytes may be used as well.

In some exemplary implementations, the continuous analyte sensor 10 may comprise a glucose sensor configured to measure glucose in the blood using one or more measurement techniques, such as enzymatic, chemical, physical, electrochemical, spectrophotometric, polarimetric, calorimetric, iontophoretic, radiometric, immunochemical, and the like. In implementations in which the continuous analyte sensor 10 includes a glucose sensor, the glucose sensor may be comprise any device capable of measuring the concentration of glucose and may use a variety of techniques to measure glucose including invasive, minimally invasive, and non-invasive sensing techniques (e.g., fluorescent monitoring), to provide a data, such as a data stream, indicative of the concentration of glucose in a host. The data stream may be raw data signal, which is converted into a calibrated and/or filtered data stream used to provide a value of glucose to a host, such as a user, a patient, or a caretaker (e.g., a parent, a relative, a guardian, a teacher, a doctor, a nurse, or any other individual that has an interest in the wellbeing of the host). Moreover, the continuous analyte sensor 10 may be implanted as at least one of the following types of sensors: an implantable glucose sensor, a transcutaneous glucose sensor, implanted in a host vessel or extracorporeally, a subcutaneous sensor, a refillable subcutaneous sensor, an intravascular sensor.

Although the description herein refers to some implementations that include a continuous analyte sensor 10 comprising a glucose sensor, the continuous analyte sensor 10 may comprises other types of analyte sensors as well. Moreover, although some implementations refer to the glucose sensor as an implantable glucose sensor, other types of devices capable of detecting a concentration of glucose and providing an output signal representative of glucose concentration may be used as well. Furthermore, although the description herein refers to glucose as the analyte being measured, processed, and the like, other analytes may be used as well including, for example, ketone bodies (e.g., acetone, acetoacetic acid and beta hydroxybutyric acid, lactate, etc.), glucagon, Acetyl Co A, triglycerides, fatty acids, intermediaries in the citric acid cycle, choline, insulin, cortisol, testosterone, and the like.

Figure 2:
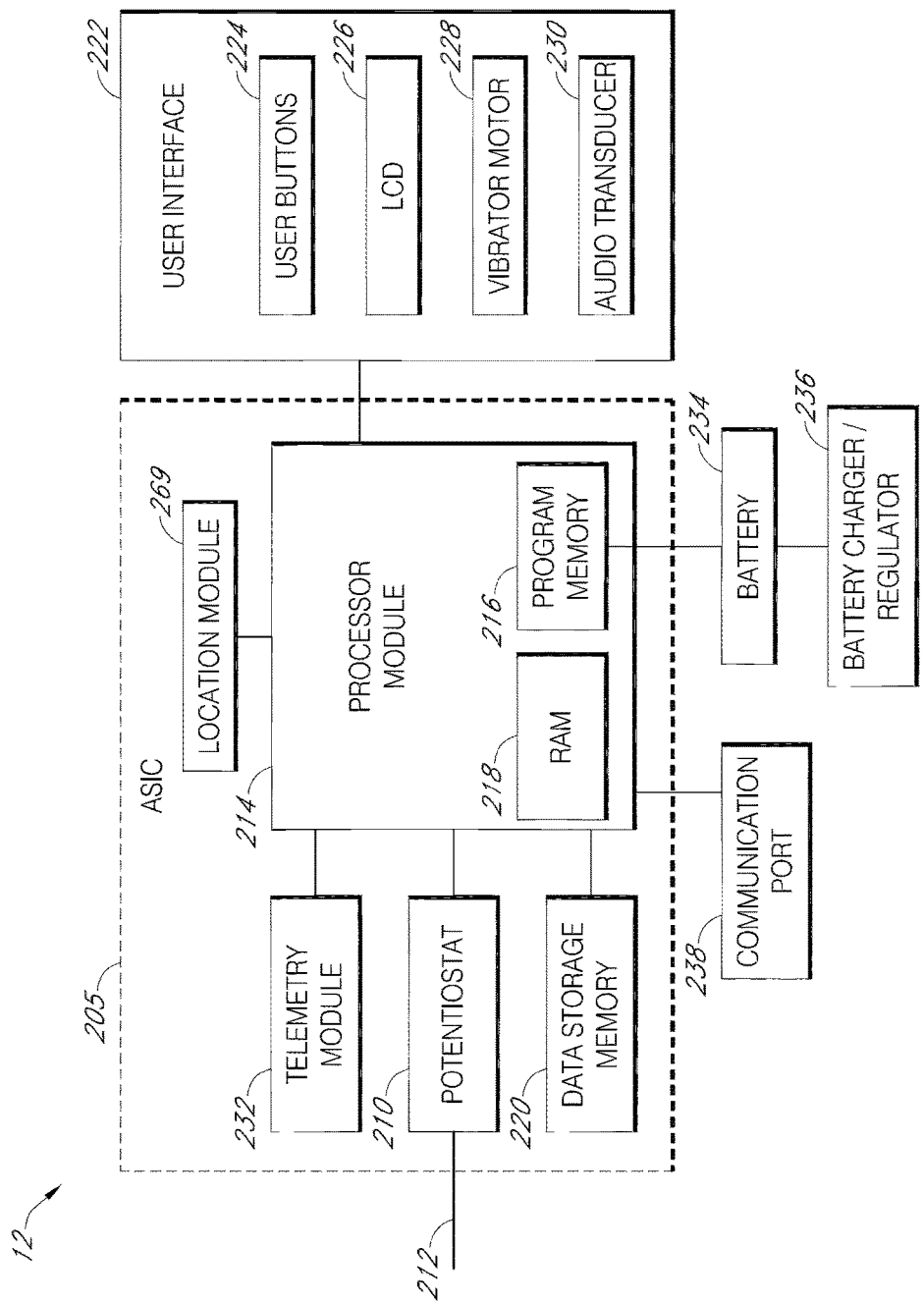
FIG. 2 depicts a block diagram illustrating the sensor electronics module in accordance with some exemplary implementations.

FIG. 2 depicts an example of a sensor electronics module 12, in accordance with some exemplary implementations. The sensor electronics module 12 may include sensor electronics that are configured to process sensor information, such as sensor data, and generate transformed sensor data and displayable sensor information. For example, the sensor electronics module may transform sensor data into one or more of the following: filtered sensor data (e.g., one or more filtered analyte concentration values), raw sensor data, calibrated sensor data (e.g., one or more calibrated analyte concentration values), rate of change information, trend information, rate of acceleration information, sensor diagnostic information, location information (which may be provided by a location module 269 providing location information, such as global positioning system information), alarm/alert information, calibration information, smoothing and/or filtering algorithms of sensor data, and/or the like.

In some exemplary implementations, the sensor electronics module 12 may be configured to calibrate the sensor data, and the data storage memory 220 may store the calibrated sensor data points as transformed sensor data. Moreover, the sensor electronics module 12 may be configured, in some exemplary implementations, to wirelessly receive calibration information from a display device, such as devices 14, 16, 18, and/or 20, to enable calibration of the sensor data from sensor 12 and data line 212. Furthermore, the sensor electronics module 12 may be configured to perform additional algorithmic processing on the sensor data (e.g., calibrated and/or filtered data and/or other sensor information), and the data storage memory 220 may be configured to store the transformed sensor data and/or sensor diagnostic information associated with the algorithms.

In some exemplary implementations, the sensor electronics module 12 may comprise an application-specific integrated circuit (ASIC) 205 coupled to a user interface 122. The ASIC 205 may further include a potentiostat 210, a telemetry module 232 for transmitting data from the sensor electronics module 12 to one or more devices, such devices 14, 16, 18, and/or 20, and/or other components for signal processing and data storage (e.g., processor module 214 and data store 220). Although FIG. 2 depicts ASIC 205, other types of circuitry may be used as well, including field programmable gate arrays (FPGA), one or more microprocessors configured to provide some (if not all of) the processing performed by the sensor electronics module 12, analog circuitry, digital circuitry, or a combination thereof.

In the example depicted at FIG. 2, the potentiostat 210 is coupled to a continuous analyte sensor 10, such as a glucose sensor, via data line 212 to receive sensor data from the analyte. The potentiostat 210 may also provide via data line 212 a voltage to the continuous analyte sensor 10 to bias the sensor for measurement of a value (e.g., a current and the like) indicative of the analyte concentration in a host (also referred to as the analog portion of the sensor). The potentiostat 210 may have one or more channels (and corresponding one or more data lines 212), depending on the number of working electrodes at the continuous analyte sensor 10.

In some exemplary implementations, the potentiostat 210 may include a resistor that translates a current value from the sensor 10 into a voltage value, while in some exemplary implementations, a current-to-frequency converter may also be configured to integrate continuously a measured current value from the sensor 10 using, for example, a charge-counting device. In some exemplary implementations, an analog-to-digital converter may digitize the analog signal from the sensor 10 into so-called "counts" to allow processing by the processor module 214. The resulting counts may be directly related to the current measured by the potentiostat 210, which may be directly related to an analyte level, such as a glucose level, in the host.

The telemetry module 232 may be operably connected to processor module 214 and may provide the hardware, firmware, and/or software that enable wireless communication between the sensor electronics module 12 and one or more other devices, such as display devices, processors, network access devices, and the like. A variety of wireless radio technologies that can be implemented in the telemetry module 232 include Bluetooth, Bluetooth Low-Energy, the ANT protocol, NFC (near field communications), ZigBee, IEEE 802.11, IEEE 802.16, cellular radio access technologies, radio frequency (RF), infrared (IR), paging network communication, magnetic induction, satellite data communication, spread spectrum communication, frequency hopping communication, near field communications, and/or the like. In some exemplary implementations, the telemetry module 232 comprises a Bluetooth chip, although the Bluetooth technology may also be implemented in a combination of the telemetry module 232 and the processor module 214.

The processor module 214 may control the processing performed by the sensor electronics module 12. For example, the processor module 214 may be configured to process data (e.g., counts), from the sensor, filter the data, calibrate the data, perform fail-safe checking, and/or the like.

In some exemplary implementations, the processor module 214 may comprise a digital filter, such as for example an infinite impulse response (IIR) or a finite impulse response (FIR) filter. This digital filter may smooth a raw data stream received from sensor 10, data line 212 and potentiostat 210 (e.g., after the analog-to-digital conversion of the sensor data). Generally, digital filters are programmed to filter data sampled at a predetermined time interval (also referred to as a sample rate). In some exemplary implementations, such as when the potentiostat 210 is configured to measure the analyte (e.g., glucose and the like) at discrete time intervals, these time intervals determine the sampling rate of the digital filter. In some exemplary implementations, the potentiostat 210 is configured to measure continuously the analyte, for example, using a current-to-frequency converter. In these current-to-frequency converter implementations, the processor module 214 may be programmed to request, at predetermined time intervals (acquisition time), digital values from the integrator of the current-to-frequency converter. These digital values obtained by the processor module 214 from the integrator may be averaged over the acquisition time due to the continuity of the current measurement. As such, the acquisition time may be determined by the sampling rate of the digital filter.

The processor module 214 may further include a data generator configured to generate data packages for transmission to devices, such as the display devices 14, 16, 18, and/or 20. Furthermore, the processor module 215 may generate data packets for transmission to these outside sources via telemetry module 232. In some exemplary implementations, the data packages may, as noted, be customizable for each display device, and/or may include any available data, such as a time stamp, displayable sensor information, transformed sensor data, an identifier code for the sensor and/or sensor electronics module, raw data, filtered data, calibrated data, rate of change information, trend information, error detection or correction, and/or the like.

The processor module 214 may also include a program memory 216 and other memory 218. The processor module 214 may be coupled to a communications interface, such as a communication port 238, and a source of power, such as a battery 234. Moreover, the battery 234 may be further coupled to a battery charger and/or regulator 236 to provide power to sensor electronics module 12 and/or charge the batteries 234.

The program memory 216 may be implemented as a semi-static memory for storing data, such as an identifier for a coupled sensor 10 (e.g., a sensor identifier (ID)) and for storing code (also referred to as program code) to configure the ASIC 205 to perform one or more of the operations/functions described herein. For example, the program code may configure processor module 214 to process data streams or counts, filter, calibrate, perform fail-safe checking, and the like.

The memory 218 may also be used to store information. For example, the processor module 214 including memory 218 may be used as the system's cache memory, where temporary storage is provided for recent sensor data received from data line 212 and potentiostat 210. In some exemplary implementations, the memory may comprise memory storage components, such as read-only memory (ROM), random-access memory (RAM), dynamic-RAM, static-RAM, non-static RAM, easily erasable programmable read only memory (EEPROM), rewritable ROMs, flash memory, and the like.

The data storage memory 220 may be coupled to the processor module 214 and may be configured to store a variety of sensor information. In some exemplary implementations, the data storage memory 220 stores one or more days of continuous analyte sensor data. For example, the data storage memory may store 1, 3, 4, 5, 6, 7, 8, 9, 10, 11, 12, 13, 14, 15, 20, and/or 30 (or more days) of continuous analyte sensor data received from sensor 10 via data line 212. The stored sensor information may include one or more of the following: a time stamp, raw sensor data (one or more raw analyte concentration values), calibrated data, filtered data, transformed sensor data, and/or any other displayable sensor information.

The user interface 222 may include a variety of interfaces, such as one or more buttons 224, a liquid crystal display (LCD) 226, a vibrator 228, an audio transducer (e.g., speaker) 230, a backlight, and/or the like. The components that comprise the user interface 222 may provide controls to interact with the user (e.g., the host). One or more buttons 224 may allow, for example, toggle, menu selection, option selection, status selection, yes/no response to on-screen questions, a "turn off" function (e.g., for an alarm), a "snooze" function (e.g., for an alarm), a reset, and/or the like. The LCD 226 may provide the user with, for example, visual data output. The audio transducer 230 (e.g., speaker) may provide audible signals in response to triggering of certain alerts, such as present and/or predicted hyperglycemic and hypoglycemic conditions. In some exemplary implementations, audible signals may be differentiated by tone, volume, duty cycle, pattern, duration, and/or the like. In some exemplary implementations, the audible signal may be configured to be silenced (e.g., snoozed or turned off) by pressing one or more buttons 224 on the sensor electronics module and/or by signaling the sensor electronics module using a button or selection on a display device (e.g., key fob, cell phone, and/or the like).

Although audio and vibratory alarms are described with respect to FIG. 2, other alarming mechanisms may be used as well. For example, in some exemplary implementations, a tactile alarm is provided including a poking mechanism configured to "poke" the patient in response to one or more alarm conditions.

The battery 234 may be operatively connected to the processor module 214 (and possibly other components of the sensor electronics module 12) and provide the necessary power for the sensor electronics module 12. In some exemplary implementations, the battery is a Lithium Manganese Dioxide battery, however any appropriately sized and powered battery can be used (e.g., AAA, Nickel-cadmium, Zinc-carbon, Alkaline, Lithium, Nickel-metal hydride, Lithium-ion, Zinc-air, Zinc-mercury oxide, Silver-zinc, or hermetically-sealed). In some exemplary implementations, the battery is rechargeable. In some exemplary implementations, a plurality of batteries can be used to power the system. In yet other implementations, the receiver can be transcutaneously powered via an inductive coupling, for example.

A battery charger and/or regulator 236 may be configured to receive energy from an internal and/or external charger. In some exemplary implementations, a battery regulator (or balancer) 236 regulates the recharging process by bleeding off excess charge current to allow all cells or batteries in the sensor electronics module to be fully charged without overcharging other cells or batteries. In some exemplary implementations, the battery 234 (or batteries) is configured to be charged via an inductive and/or wireless charging pad, although any other charging and/or power mechanism may be used as well.

One or more communication ports 238, also referred to as external connector(s), may be provided to allow communication with other devices, for example a personal computer (PC) communication (com) port can be provided to enable communication with systems that are separate from, or integral with, the sensor electronics module. The communication port, for example, may comprise a serial (e.g., universal serial bus or "USB") communication port, to communicate with another computer system (e.g., PC, personal digital assistant or "PDA," server, or the like). The communication port may also be coupled to a wireless transceiver to allow wireless communications as well. In some exemplary implementations, the sensor electronics module 12 is able to transmit historical data to a PC or other computing device (e.g., an analyte processor as disclosed herein) for retrospective analysis by a patient and/or physician.

In some continuous analyte sensor systems, an on-skin portion of the sensor electronics may be simplified to minimize complexity and/or size of on-skin electronics, for example, providing only raw, calibrated, and/or filtered data to a display device configured to run calibration and other algorithms required for displaying the sensor data. However, the sensor electronics module 12 may be implemented to execute prospective algorithms used to generate transformed sensor data and/or displayable sensor information, including, for example, algorithms that: evaluate a clinical acceptability of reference and/or sensor data, evaluate calibration data for best calibration based on inclusion criteria, evaluate a quality of the calibration, compare estimated analyte values with time corresponding measured analyte values, analyze a variation of estimated analyte values, evaluate a stability of the sensor and/or sensor data, detect signal artifacts (noise), replace signal artifacts, determine a rate of change and/or trend of the sensor data, perform dynamic and intelligent analyte value estimation, perform diagnostics on the sensor and/or sensor data, set modes of operation, evaluate the data for aberrancies, and/or the like.

Although separate data storage and program memories are shown in FIG. 2, a variety of configurations may be used as well. For example, one or more memories may be used to provide storage space to support data processing and storage requirements at sensor electronic module 12.

Figure 3:
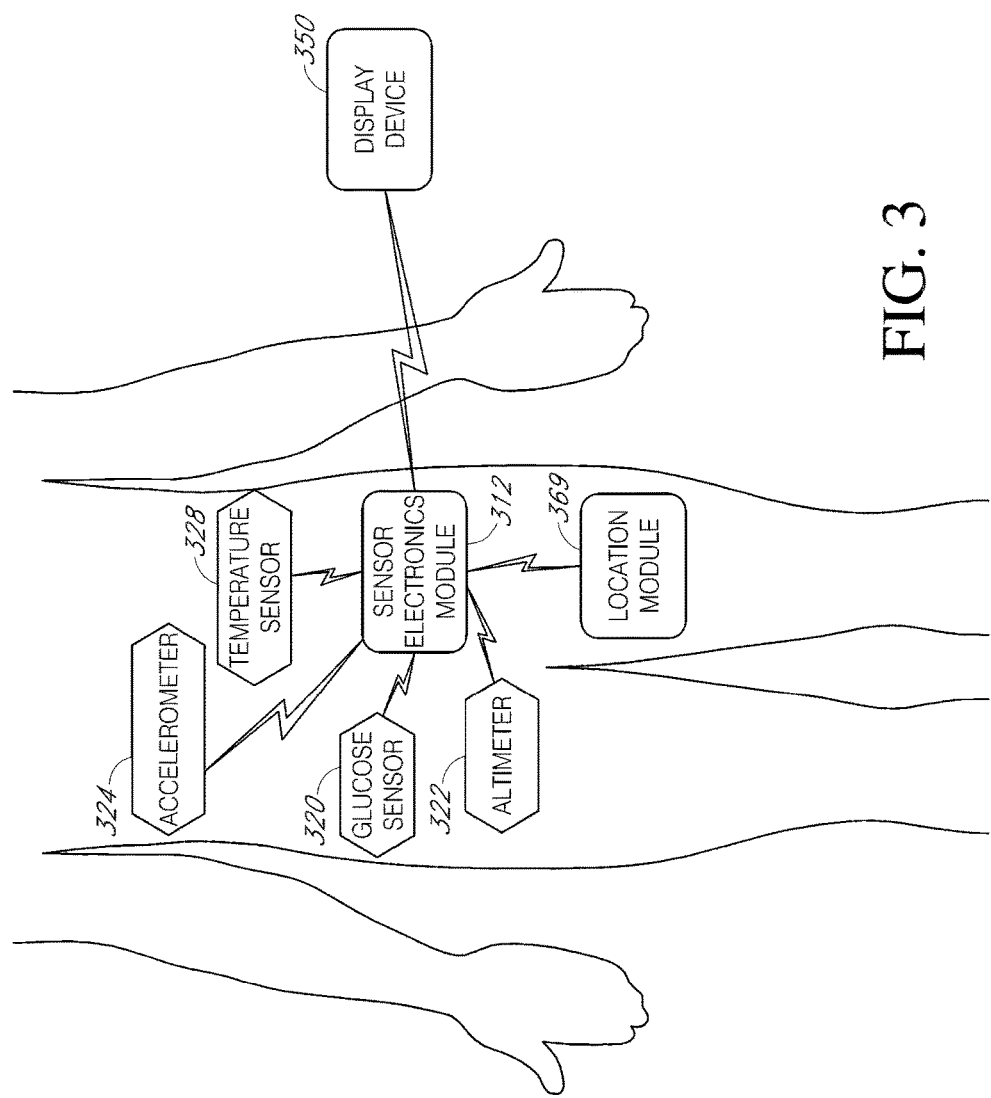
FIG. 3 depicts a block diagram illustrating the sensor electronics module communicating with multiple sensors, including a glucose sensor in accordance with some exemplary implementations.

FIG. 3 depicts an example a diagram illustrating sensor electronics module 312 in communication with multiple sensors, including a glucose sensor 320, an altimeter 322, an accelerometer 324, a temperature sensor 328, and a location module 369 (e.g., a global positioning system processor or other source of location information) in accordance with some exemplary implementations. Although FIG. 3 depicts sensor electronics module 312 in communication with specific sensors, other sensors and devices may be used as well including, for example, heart rate monitors, blood pressure monitors, pulse oximeters, caloric intake, medicament delivery devices, and the like. Moreover, one or more of these sensors may provide data to the analyte processing system 400 and/or analyte processor 490 via data retriever 465 described further below. In some implementations, a user may manually provide some of the data to analyte processing system 400 and/or analyte processor 490. For example, a user may provide calories consumed information via a user interface to analyte processing system 400 and/or analyte processor 490.

In the example depicted at FIG. 3, each of the sensors 320-328 communicates sensor data wirelessly to the sensor electronics module 312. In some exemplary implementations, the sensor electronics module 312 includes one or more of the sensors 320-328. In some exemplary implementations, the sensors are combined in any other configuration, such as a combined glucose/temperature sensor that transmits sensor data to the sensor electronics module 312 using common communication circuitry. Depending on the embodiment, fewer or additional sensors may communicate with the sensor electronics module 312. In some exemplary implementations, one or more of the sensors 320-328 is directly coupled to the sensor electronics module 312, such as via one or more electrical communication wires.

The sensor electronics module 312 may generate and transmit, via a wireless or wired medium, a data package to a device, such as display device 350, a processor including data retriever 465, and the like configured to receive, store, forward/retransmit, and/or display displayable sensor data. The sensor electronics module 312 may analyze the sensor data from the multiple sensors and determine which displayable sensor data is to be transmitted based on one or more of many characteristics of the host, the display device 350, a user of the display device 350, and/or characteristics of the sensor data. Thus, the customized displayable sensor information that is transmitted to a device, such as the display device 350, may be displayed on the device with minimal processing by the device.

Figure 4A:
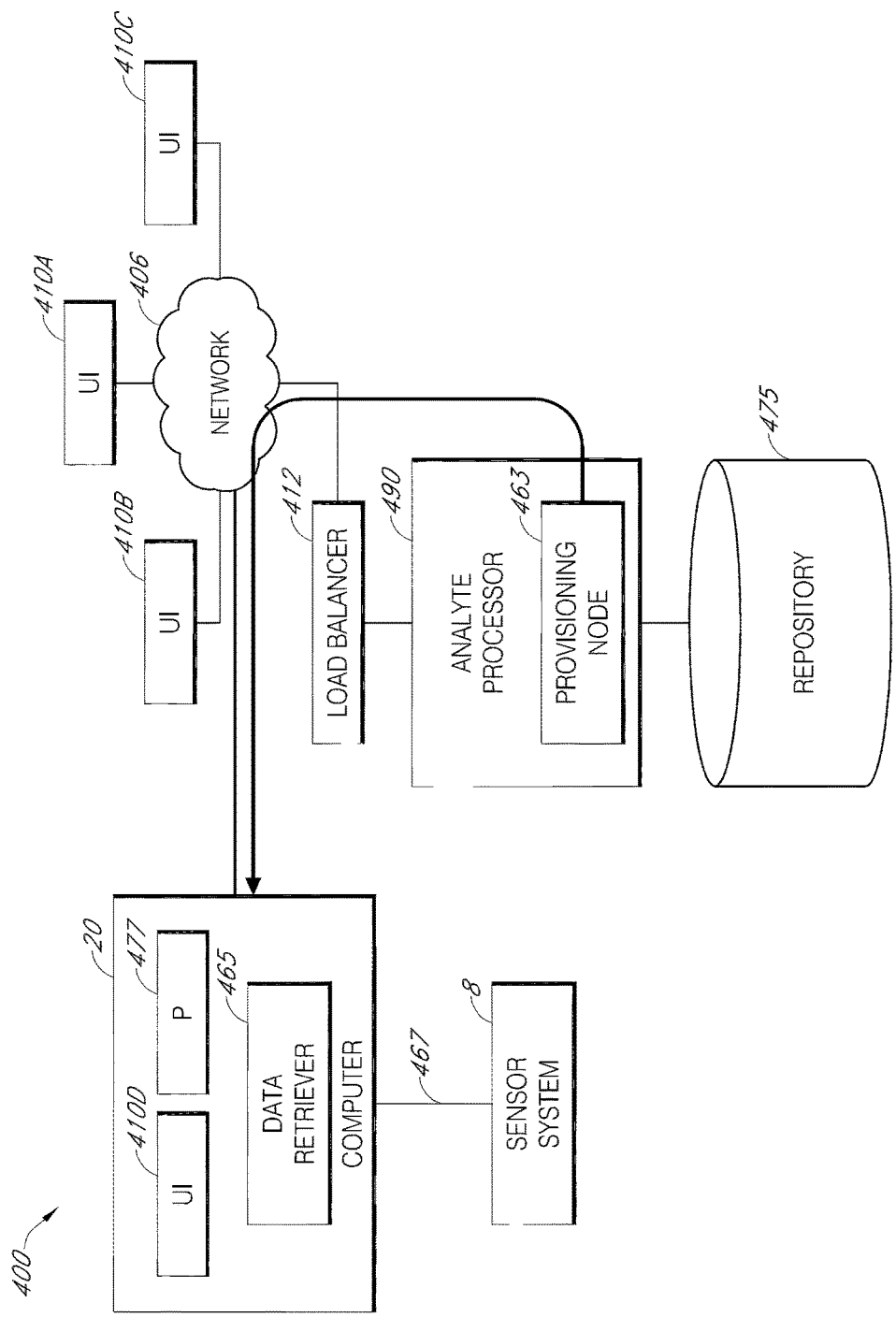
FIGS. 4A, 4B, and 4C depict block diagrams of an analyte processing system in accordance with some exemplary implementations.

FIG. 4A depicts an example of an analyte data processing system 400, in accordance with some exemplary implementations. The analyte data processing system 400 may include one or more user interfaces 410A-D, such as a browser, an application, and/or any other type of interface (e.g., programming interfaces, system-to-system interfaces, and the like) configured to allow accessing and/or interacting with analyte processor 490 via, for example, network 406 and a load balancer 412. The analyte processor 490 may be further coupled to a repository, such as repository 475. The system 400 may also include a data retriever 465 interfacing sensor system 8 and the analyte processor 490, and the analyte processor 490 may further include a provisioning node 463 configured to provide data, such as software, drivers, plug-ins and the like, during installation including upgrades of data retriever 465. The provisioning node 463 may also provide security credentials that define authentication and authorization required to perform an update, and, in some example, implementations, the security credentials may be generated uniquely for a given installation instance of a host-user, sensor system 8, data retriever 465, and the like. The provisioning node 463 may facilitate other configuration options, such as retrieval of diagnostic data, gathering streaming data from a sensor, enabling user-adjustable configurations, such as a blind mode, an unblind mode, a purging mode to clear data from the persistent storage of devices associated with the sensor system 8, setting a clock of the sensor system, and the like. These configuration options can be preselected so the options are automatically configured upon the occurrence of a triggering action, such as selecting a registration input, connecting a sensor system device to the provisioning node, and the like.

The analyte data processing system 400 may provide a cloud-based diabetes data management framework that receives patient-related data from various devices, such as a medical device, a glucose meter, a continuous glucose monitor, sensor system 8, display devices 14-20, source systems, and/or other devices (e.g., a device providing food consumption, such as carbohydrates, consumed by a host or patient, medicament delivery data, time of day, temperature sensors, exercise/activity sensors, and the like). In some exemplary implementations, the cloud-based diabetes data management system may receive the data programmatically with little (or no) intervention on the part of a user. The data received from devices, source systems, and the like may be in a variety of formats and may be structured or unstructured. For example, the analyte processor 490 may receive, from sensor system 8 and data retriever 465, raw sensor data, which has been minimally processed or analyzed, and the received data is then formatted, processed (e.g., analyzed), and/or stored in order to enable report generation by analyte processor 490. In addition to sensor data, analyte data processing system 400 may also receive data from source systems, such as health care management systems, patient management systems, prescription management systems, electronic medical record systems, personal health record systems, and the like.

The user interfaces 410A-D may be used by one or more entities, such as end-users, hosts, health care providers, clinics, patients, research groups, health systems, medical device manufacturers, and the like. These entities may remotely access analyte processor 490 via user interface 410A-D to request an action, such as retrieve analyte data, provide analyte data, request analysis of analyte data, request generation of reports including descriptive measurements of the analyte data, present analyte data and reports, and the like. For example, user interface 410A may send a request (e.g., a message and the like) to initiate an action at an analyte processor 490, which is remote (e.g., separate from the user interfaces and coupled by a network). The action may request a report for the sensor data provided by data retriever 465. Other examples of actions include providing sensor data, such as glucose data, carbohydrate data, insulin pump data, and the like, to the analyte processor 490, initiating processing of the sensor data, initiating analysis of the sensor data, storing data at repository 475, registering devices and/or users at the analyte processor, requesting installation files to obtain software for the data retriever 465, and the like.

In some implementations, the data retriever 465 may be implemented at one or more devices, such as computer 20 coupled to sensor system 8. The data retriever 465 may provide sensor data generated by sensor system 8 to analyte processor 490. The data retriever 465 may, in some implementations, forward the sensor data generated by sensor system 8 as a pass-through (e.g., without persistently storing the data at computer 20, although the data may be stored in transient memory at computer 20 while waiting transmission) directly to analyte processor 490, while in some implementations, data retriever 465 may process (e.g., store, format and the like) the sensor data before sending the formatted data to analyte processor 490. In some implementations, the data retriever 465 may be accessed through a dedicated processor, such as a kiosk including computer 20 configured with data retriever 465 and user interface 410D (which may be accessed by a plurality of users), or may be accessed via a secure web-based interface residing on computer 20 configured as a non-dedicated device including the data retriever 465 and user interface 410D (e.g., located at a user's home computer and the like).

Although FIG. 4A depicts data retriever 465 implemented at computer 20, data retriever 465 may be implemented in other devices, such as sensor system 8, sensor 10, display devices 14, 16, 18, and/or 20, medicament pump 2, glucose meter 4, computers/processors coupled to those devices, telecommunications devices, networking devices, and any other device capable of providing data to system 400. In these implementations, data retriever 465 may receive data from a host device and forward the sensor data to analyte processor 490. The data retriever 465 may also be implemented on source systems, such as disease management systems, weight management systems, prescription management systems, electronic medical records systems, personal health record systems, and the like. In these implementations, data retriever 465 obtains, as noted, data from the source system and forwards the data to analyte processor 490.

The data retriever 465 may be implemented as an application stored in memory, which when executed by computer 20, provides the data retriever 465. In some implementations, the data retriever 465 may be implemented as a widget, although other types of implementations may also be used as well.

In some implementations, the data retriever 465 may generate a page for presentation at user interface 410D, which may show that computer 20 is accessing and retrieving data from sensor system 8. For example, the page may show the status of the data transfer from the sensor system 8 and/or to the analyte processor 490, although the transfers may be performed without providing the status information on a page presented to a user.

Figure 5A:
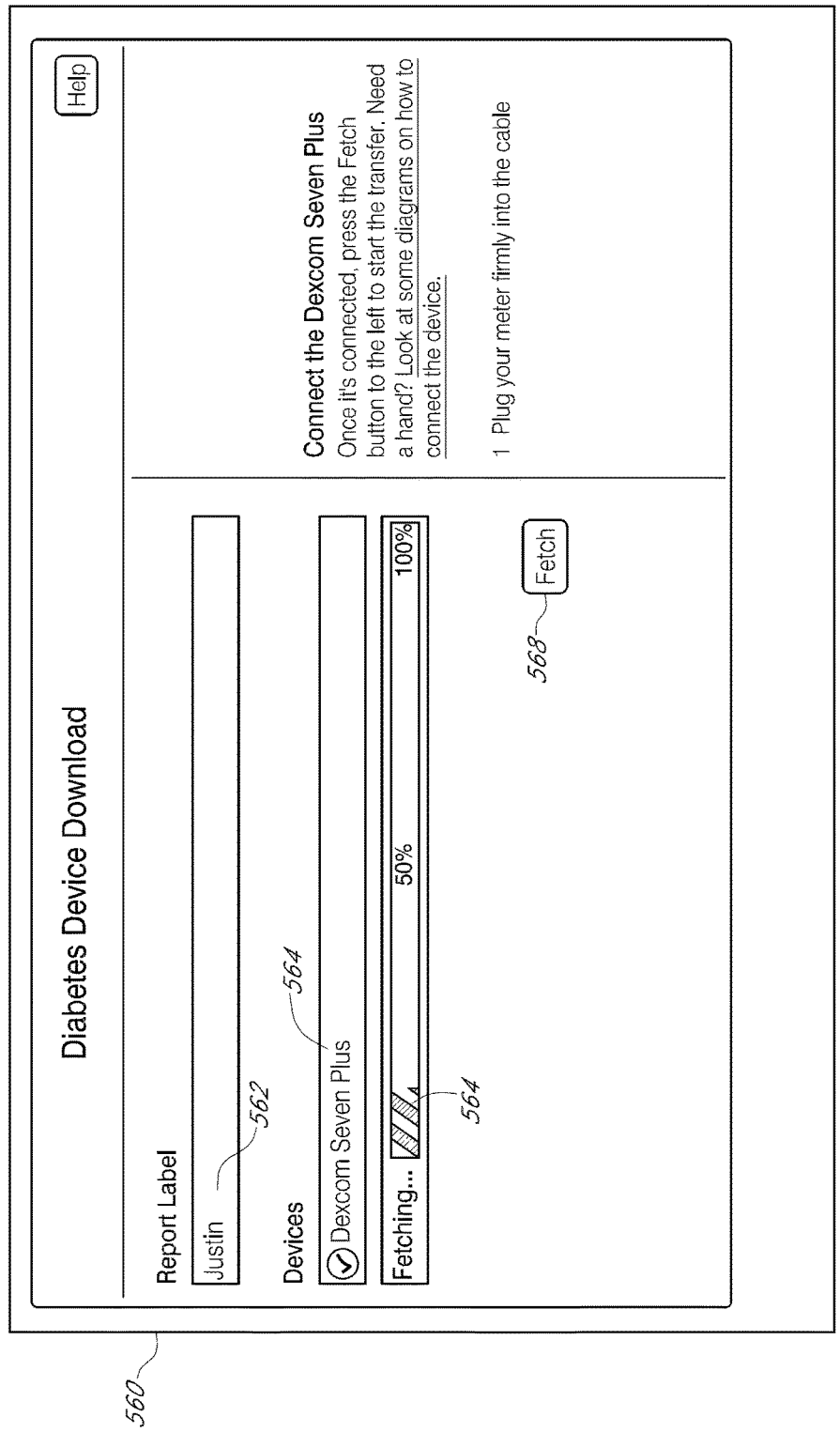
FIGS. 5A and 5B depict example pages presented during the download installation process of a data retriever, in accordance with some exemplary implementations.

FIG. 5A depicts a page 560 presented at, for example, the user interface 410D. The page 560 allows a user to enter the identity of the patient 562 and the device identity/type 564 coupled to the computer 20 including the data retriever 465. In some implementations, the data retriever 465 determines the device identity/type 564 (e.g., "DexCom Seven Plus") programmatically, while in others, a user enters the device identity/type 564. In any case, when the user is ready to receive information from the sensor system (which in this example is a "DexCom Seven Plus"), the user may select Fetch 568 to begin the process, although in some implementations the fetching may begin when the device, such as sensor system 8, couples (e.g., via a wireless or wired link(s)) to the computer 20 without requiring the selection of icon 568. The status of the transfer of data from the sensor system 8 to the data retriever 465 may also be presented as a graphical element, such as a bar 566. In this example, the bar 566 increases in length as the download proceeds and when completed reaches the 100% point.

Referring again to FIG. 4A, the first time a processor, such as computer 20, a smart phone, a tablet, and any other device including at least one processor and at least one memory, accesses analyte processor 490, the data retriever software may be programmatically installed on the processor by downloading data including the data retriever software, a plug-in, and/or configuration/installation information to the processor's memory. For example, analyte processor 490 may be coupled to a network, such as the Internet, and when computer 20 accesses the analyte processor 490 (e.g., before data retriever is installed on computer 20), a user may be presented with an icon or other graphical element at computer 20 to initiate a download of an installation package including data retriever software, a plug-in, and/or configuration/installation information, which when installed and executed provides data retriever 465.

Moreover, provisioning node 463 may control aspects of the download as described herein and may include data, such as data retriever software, one or more versions of the data retriever software, drivers, install files, plug-ins, configuration data, and the like, which when downloaded, installed, and executed at computer 20 provides data retriever 465 and/or a plug-in 477 (also referred to herein as a retriever plug-in). The configuration data may include security credentials that define authentication and authorization required to perform an update and may be generated uniquely for a given installation instance of a host-user, sensor system 8, data retriever 465, and the like. In some implementations, retriever plug-in 477 works in conjunction with the data retriever 465 (and its business logic) to perform operations such as installing, updating, and the like. In any case, the downloaded data including software and the like may occur by, for example, programmatically installing the software on the processor, such as computer 20.

Figure 5B:
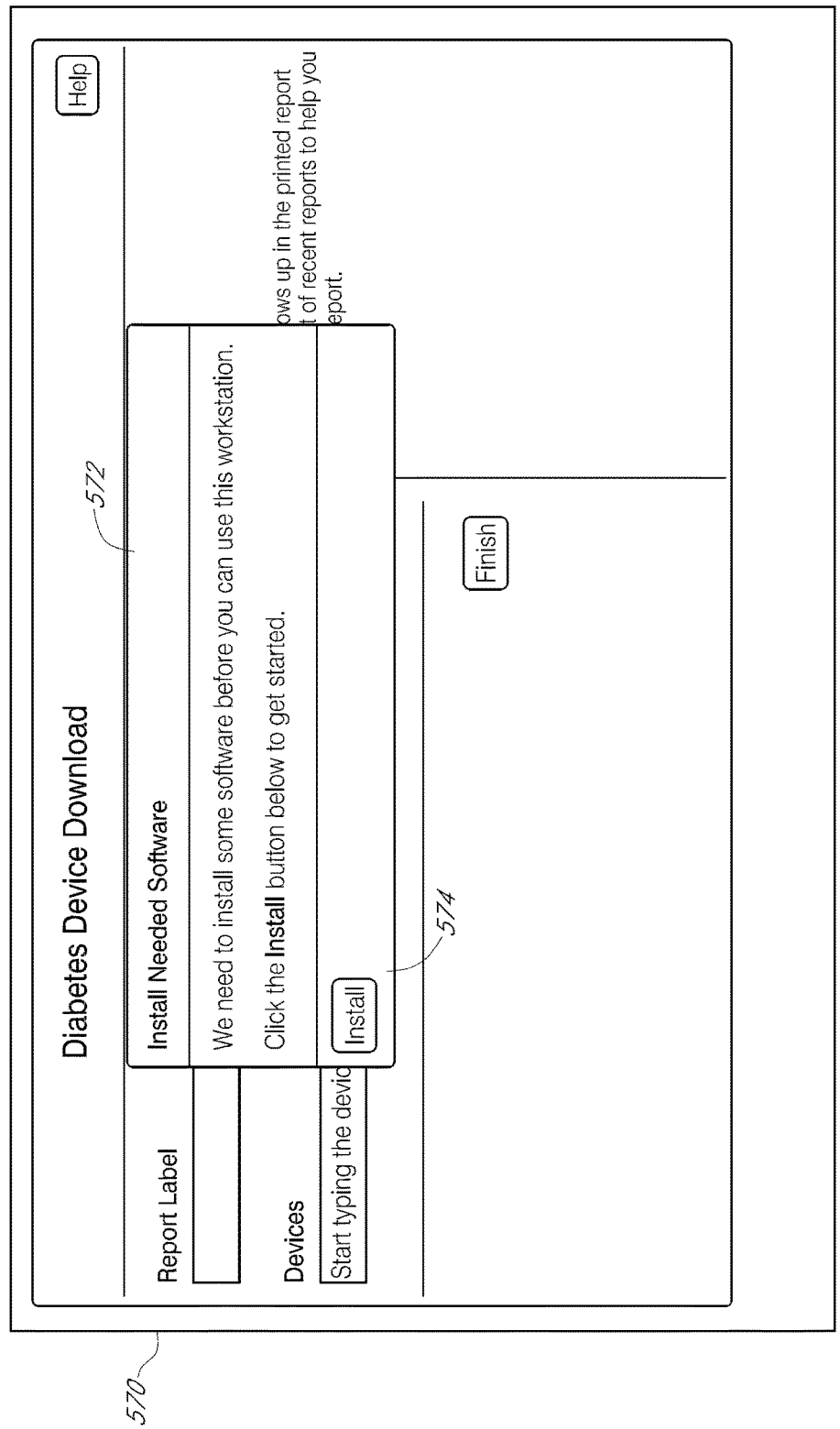

FIG. 5B depicts an example of a page 570 presented at, for example, user interface 410D, when computer 20 accesses analyte processor 490 without having data retriever software installed on computer 20. The page 570 includes information 572 that the data retriever software is being loaded from the provisioning node 463 to the computer 20.

Referring again to FIG. 4A, the retriever plug-in 477 may be delivered and retrieved from the installation package downloaded from the analyte processor 490. The retriever plug-in 477 may be installed as part of a client installer at computer 20 (e.g., an installer provided by the operating system and/or a dedicated installer). In some implementations, the retriever plug-in 477 may be installed programmatically without going through a plurality of installation pages that guide a user through the process, and, once installed, the retriever plug-in 477 may control and/or monitor aspects of the installation of the data retriever 465. For example, a single selection of the install element 574 at page 565 of FIG. 5B may initiate the download of an install package which includes, as noted, the retriever plug-in 477, which is installed as a user interface 410D plug-in (e.g., as a browser plug-in). In these implementations, the retriever plug-in 477 may be installed at user interface 410D and control the installation of the data retriever 465 client software, with little, or no, user interaction. Moreover, when there are updates to the retriever plug-in 477 itself, the auto-update process at computer 20 may download and install the new version of the retriever plug-in 477 along with an update of the data retriever 465 client software.

When the computer 20 is shared by a plurality of users (e.g., a dedicated kiosk), the retriever plug-in 477 may be bundled, as noted, in an install package and installed in a global storage space at computer 20, where a plurality of users can access the retriever plug-in 477, without having to re-install from scratch for each user. When retriever plug-in 477 is installed globally, the retriever plug-in 477 may detect whether the data retriever 465 is installed (or a current version is installed) at computer 20 and, if not, install the data retriever software (or a current version) as described herein. Once the data retriever 465 client is downloaded and installed to the global storage space, data retriever 465 may also be installed in the storage space assigned to a registered user at computer 20, when the user does not have rights or permission to install in the global space. Moreover, the retriever plug-in 477 may remain stored in the global storage space accessible by individual users that have yet to update or install the data retriever 465 client.

When the download is complete and the data retriever software is installed at computer 20, data retriever 465 may generate a view (e.g., page 560 at FIG. 5A) or direct the user to a page at another location to allow a user to select a graphical element, such as a fetch icon causing a data fetch from sensor system 8 to computer 20/data retriever 465 and then to analyte processor 490. In some implementations, the fetch icon may be implemented as a software widget. When this is the case, the software widget may be placed on a page presented at, for example, user interface 410D, so that when the icon is selected, a fetch process is executed at computer 20. However, in some implementations, when the sensor system 8 couples via wireless or wired links to computer 20, data retriever 465 fetches sensor data from sensor system 8 automatically and/or forwards the data to analyte processor 490, without prompting the user to initiate the fetch and/or forwarding.

In some implementations, the installation at computer 20 of the data retriever 465 includes a package containing the retriever plug-in 477. In implementations using the plug-in 477, the retriever plug-in 477 may launch data retriever 465, find the location of the analyte processor 490 or the provisioning node 463, obtain information regarding the current version of the data retriever software available at analyte processor 490 and/or provisioning node 463, and compare the version number at analyte processor 490/provisioning node 463 with the version of the data retriever software currently installed at computer 20 to determine whether an update of the data retriever client software is required. In some example, implementations, the analyte processor 490/provisioning node 463 may check the manufacturer, model, serial number, and/or firmware of the sensor system 8 (and/or receiver 16), and the like to determine if the firmware of the device needs to be updated. If so, the analyte processor 490/provisioning node 463 may trigger an update of the firmware of the device, such as sensor system 8, receiver 16, and the like.

Although some of the examples refer to data retriever 465 obtaining data from sensor system 8, other devices and source system may be provide data to the data retriever 465 as well.

Although FIG. 4A depicts a single data retriever 465, four user interfaces 410A-D, a single computer 20, a single sensor system 8, a single load balancer 412, a single network 406, a single analyte processor 490, a single provisioning node 463, and a single repository, other quantities (as well as configurations) of these devices may be implemented as well.

Figure 5C:
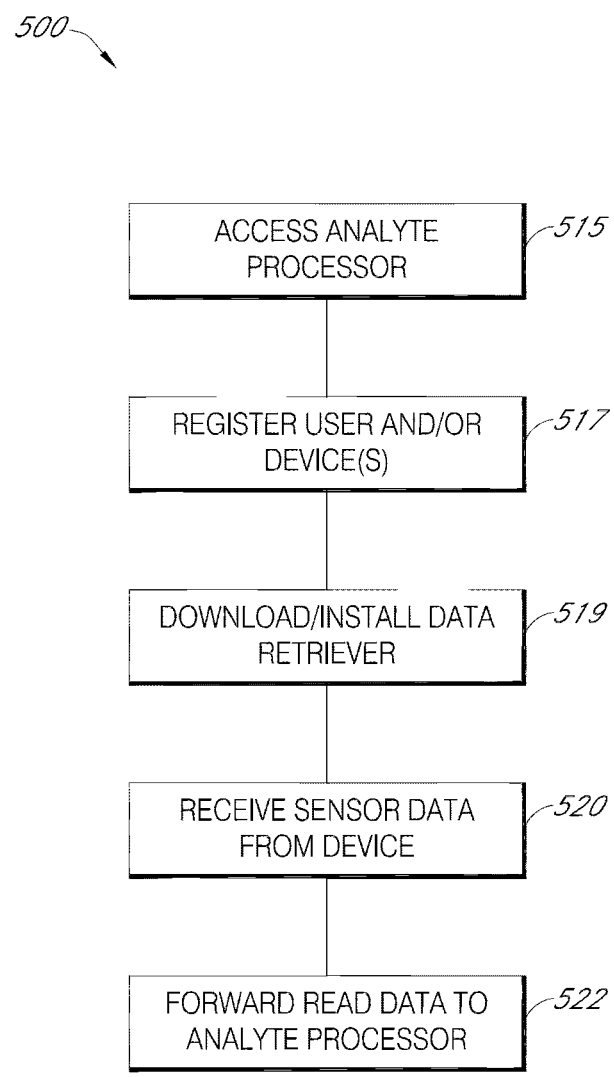
FIG. 5C depicts a process for retrieving data from a sensor in accordance with some exemplary implementations.

FIG. 5C depicts an example process 500 for installing a data retriever in a computer, in accordance with some example implementations. The description of FIG. 5C also refers to FIG. 4A.

At 515, a processor, such as computer 20, may access analyte processor 490. When a processor, such as computer 20, accesses analyte processor 490 and, in particular, provisioning node 463 responsible for managing the data retriever software download to computer 20, a user at processor 490 may initiate a download process in order to obtain software for the data retriever and install the data retriever at computer 20. For example, computer 20 may be coupled to a network, such as the Internet, and access a server providing a web site including analyte processor 490 and/or provisioning node 463. The web site may include one or more pages, which may allow the user to register for, and/or initiate, a download of the data retriever 465.

In some implementations, a user at computer 20 may also receive a link (or an address) included in a message (e.g., an email), so that when the link is selected it carries the user interface 410D to the Internet address of the web site including the analyte processor 490 and, in particular, provisioning node 463 responsible for managing the download of an install package (which may include the data retriever software, plug-in, and/or configuration information) to computer 20. Moreover, the link may include security aspects, such as a cryptographic token, that allows the user to register and then download the install package to only a certain machine, such as computer 20, or for only a certain period of time and/or a certain number of accesses (e.g., a single use link). For example, the link may have a user identified for the link, such as when the link comes from a prior host-user or a third party system, such as a hospital and the like, so registration may be required or access may be allowed without registration.

Although FIG. 4A depicts provisioning node 463 at the analyte processor 490, the provisioning node 463 may be located at other locations and/or distributed in a plurality of locations as well.

At 517, a user may register with analyte processor 490. For example, a user may provide information, such as a name, an address, and types/identities of devices coupled to computer 20 or which may provide data to analyte processor 490. Moreover, during the registration process, analyte processor 490 and, in particular, provisioning node 463 may gather information regarding the machine, such as the type of operating system at computer 20 and the like, to allow the provisioning node 463 to provide a properly configured installation package for installation at computer 20, although a user may not need to register and/or sign in to the analyte processor 490 to participate in one or more aspects of process 500.

At 519, data, such as the installation package, may be downloaded to computer 20. For example, provisioning node 403 may provide to computer 20 the installation package including data, data retriever software, a retriever plug-in, a driver, installation/configuration information, an install file, and/or the like. This data may be programmatically installed on computer 20, with little, or no, effort required by the user. Moreover, an installer may be configured on computer 20 to install the installation package and the components therein, and the installation may be performed interactively under the control of a user (or administrator), although the installation may also be performed programmatically, with little, or no, user involvement as well. For example, plug-in 477 may extract an install file from the installation package downloaded to computer 20 from the provisioning node 463, and then provide the install file to a client installer at computer 20 to perform the installation. In some implementations, the plug-in is a software plug-in application to one or more commercially available Internet browser software applications that provides the data retriever 465 functionality described herein to the browser.

At 520, the computer including the data retriever 465 may receive data, such as sensor data and the like, from a coupled device. In some implementations, computer 20 including data retriever 465 may determine what devices are coupled either via wired or wireless links to computer 20. For example, data retriever 465 may send a message (e.g., a command and the like) to sensor system 8 and read the response from sensor system 8 to determine whether sensor data from sensor system 8 can be read by computer 20. If so, computer 20 may receive data from sensor system 8 by sending a request to sensor system 8 to begin sending sensor data to computer 20 or by retrieving the data directly from sensor system 8. In either case, computer 20 including data retriever 465 may receive sensor data from sensor system 8.

At 522, computer 20 including data retriever 465 may forward the received sensor data to analyte processor 490. In some implementations, the data retriever 465 may forward the sensor data to analyte processor 490 in a pass-through mode in which the computer 20 including data retriever 465 do not persistently store, at computer 20, the sensor data and/or any corresponding personal identifiable information (PII) for the user coupled to the sensor system 8. Moreover, the pass-through mode may include coding (or encryption) to form a secure tunnel through the computer 20.

Moreover, computer 20 including data retriever 465 may forward the sensor data to analyte processor 490 in a structured way, such as a message. For example, sensor system 8 may package sensor data into a message sized sufficiently small so that the message can be processed by computer 20 and sent to analyte processor 490 with little, or no, buffering at computer 20. For example, analyte sensor 8 may package the sensor data in an eXtensible markup language format sized in order to be received at computer 20 and forwarded to analyte processor 490. The size of the packaged data may be selected (by for example the analyte processor 490) based on a volume of data generated by the sensor system 8, a capacity of the links to (and from) the computer 20, a processing speed of the computer 20, and/or a processing speed of the analyte processor 490. For example, slower processing speeds would require a smaller sized package of sensor data, when compared to faster processing speeds at computer 20 in order to avoid requiring persistent storage and/or buffering at computer 20.

In some implementations, the data retriever software downloaded to computer 20 may be updated, and this software updating may be performed as part of an automatic self-updating mechanism. For example, when a fetch is selected at the user interface 410D, data retriever 465 (or a plug-in) may programmatically check for an update (e.g., software, drivers, plug-ins, data, and the like) at analyte processor 490 and/or provisioning node 463. In addition, if a more current version of the data retriever software is available for use, computer 20 may download the newer version of data retriever software and then install the data retriever software at computer 20 as part of an update.

In some implementations, the data retriever software downloaded to computer 20 may programmatically collect and report diagnostic information to analyte processor 490 for use by administrator of the system to resolve issues with the data retrieval process. The diagnostic information can include driver software being used by computer 20, in particular any driver software in conflict with the data retriever software, and other devices in use with computer 20 (e.g., electrically and/or communicatively connected to the computer). The data retriever software update may be performed programmatically with little, or no, intervention by a user. For example, the data retriever 465 and/or the plug-in 477 may periodically poll provisioning node 463 for another version (e.g., updates, newer version, patches, fixes, and the like) of the data retriever software. And, this polling may be performed in the background without prompting the user at computer 20. When another version is identified at provisioning node 463, computer 20 may automatically download and install the other version in the background without prompting the user, so that during the next start of the data retriever 465 and/or plug-in 477, the updated/newer version of the data retriever 465 is implemented at computer 20. Although the previous example describes background updates, data retriever 465 and/or plug-in 477 may also check for updated/newer versions of the data retriever software when prompted by a user at computer 20, when the user allows automatic updates, and/or when a user requests the automatic update. Furthermore, the data retriever 465 and/or a plug-in 477 may also check for updated/newer versions at provisioning node 463 whenever the analyte processor 490 is accessed.

Figure 5D:
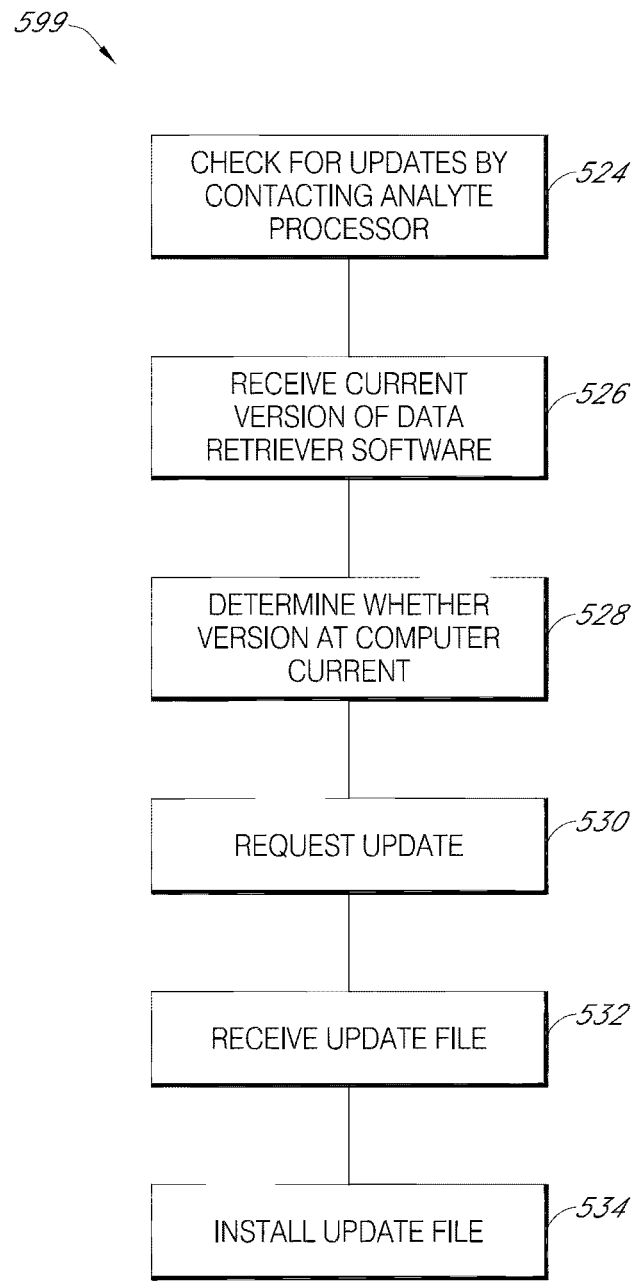
FIG. 5D depicts a process for updating software in accordance with some exemplary implementations.

FIG. 5D depicts an example process 599 for automatically updating the data retriever software being used at a processor. The description of FIG. 5D also refers to FIG. 4A.

At 524, the computer 20 may check for updates. For example, computer 20 (or data retriever 465 and/or plug-in 477 therein) may send a message to analyte processor 490 via a network, such as the Internet, to obtain the current version of the data retriever software at provisioning node 463.

At 526, the computer 20 may receive the current version of data retriever software. For example, plug-in 477 and/or data retriever 465 may receive the current version of the data retriever software at provisioning node 463.

At 528, the computer 20 may determine the current version of the data retriever software. For example, plug-in 477 and/or data retriever 465 may compare the current version received at 524 with the version currently being used at data retriever 465. For example, if the comparison indicates that there is a newer version of the data retriever software at provisioning node 463, the computer 20 may prompt the user if an updated/newer version should be retrieved (although the updated/newer version may proceed in some implementations without prompting the user).

At 530, the computer 20 may request from provisioning node 463 another version (e.g., a newer version, an update, a patch, and the like) of the data retriever software. For example, computer 20 may include a client updater (which may be a dedicated updater or part of the operating system) to receive and/or retrieve the other version and download the other version when it is received at 532. In addition, when the update is received, the updater may install, at 534, the data retriever software, so that it can be executed at computer 20. In some implementations, the plug-in 477 executes an install file received from the provisioning node 463 to allow performing the installation of the data retriever software. For example, the install file may include data, such as code, configuration information, drivers, and an install file, to allow execution of the installation by a client updater.

In some implementations, the plug-in may determine the identity of the user. For example, if the user is an administrator (e.g., assigned admin privileges at system 400), the installation package (which may include the data retriever client software and the like) may be installed in a global storage space at computer 20, so that the install package may be accessible by a plurality of other users in order to allow updating. However, if the user is not a so-called administrator, the installation package may be installed in a user storage location. For example, the plug-in 477 may initiate an update of the more current data retriever software using either the current version stored in global storage or obtain a copy from analyte processor 490 (which may be stored in a user storage space rather than a global one).

In some implementations, analyte processor 490 may send a command to configure computer 20 and/or sensor system 8 in a blind mode. As used herein, blind mode refers to configuring computer 20 and/or sensor system 8 such that those device forward data to analyte processor 490 in a manner that does not allow the user to view (and/or access, store, or handle) the forwarded data at computer 20 and/or sensor system 8. The blind mode of computer 20 and/or sensor system 8 may be useful when the user coupled to sensor system 8 is wearing device 8 for a limited time and thus may not have the training to understand how to read, interpret, and the like the data gather by computer 20 and/or sensor system 8. Moreover, the blind mode may configure sensor system 8 so that it can be used by various users without disclosing heath-related data.

Figure 5E:
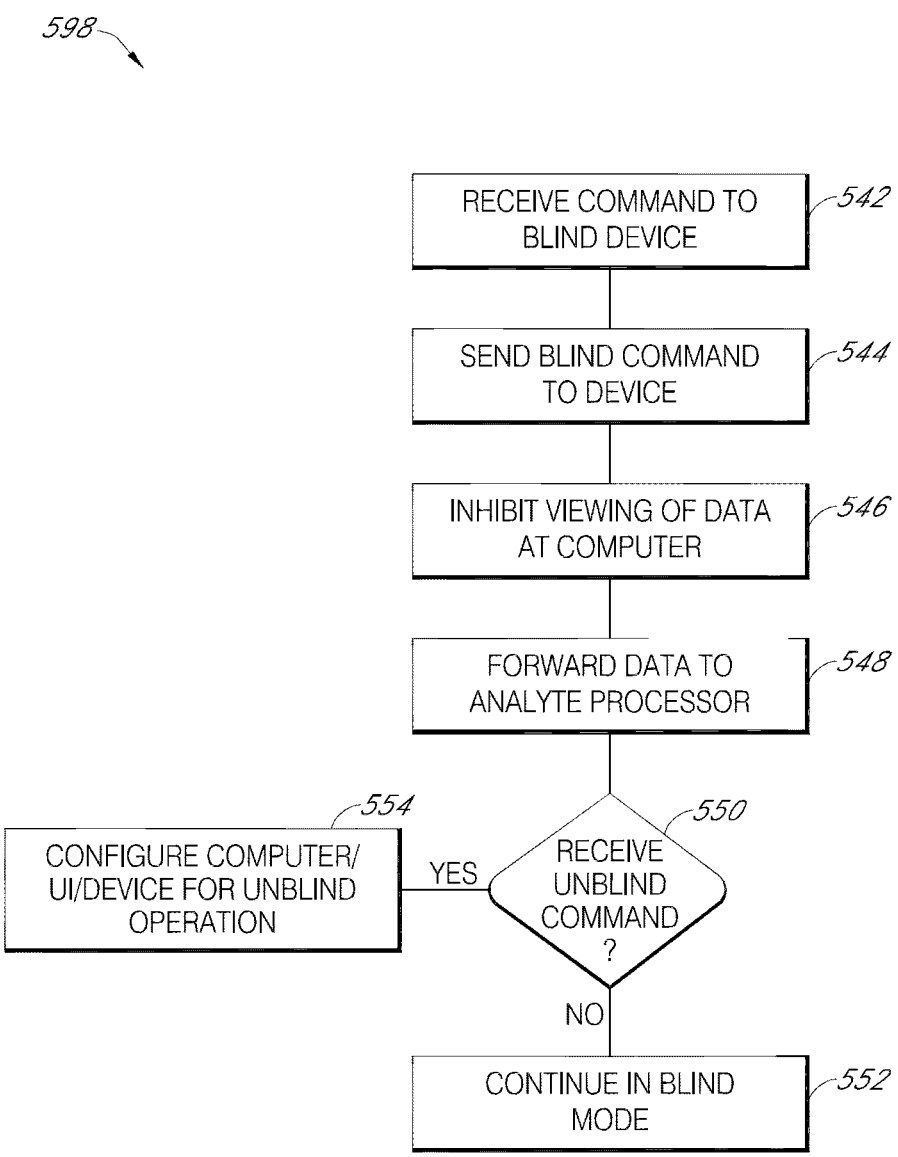
FIG. 5E depicts a process for placing a sensor in a blind mode in accordance with some exemplary implementations.

FIG. 5E depicts an example of a process 598 for placing computer 20 and/or sensor system 8 in a blind mode in accordance with some exemplary implementations. The description of FIG. 5D also refers to FIG. 4A.

In some example implementations, the blind mode may be configured at the sensor system, the computer, or a combination of both. For example, a clinic may blind sensor system 8 provided on a temporary basis to a host-patient coupled to the sensor system 8, but in this example the clinic may access a computer 20 to view the data from sensor system 8 so the sensor system 8 is blinded but the computer 20 is not blinded. To illustrate with another example, a research trial may configure blind mode at both the sensor system and the computer 20.

In some implementations, one or more of the connections between the sensor system 8, computer 20, and/or the analyte processor 490 may be encrypted, authenticated, and authorized when health-related data is being carried over the connections.

At 542, computer 20 may receive an indication, such as a command, a message, and the like, that computer 20 and/or sensor system 8 should enter a blind mode. For example, analyte processor 490 may send a message to computer 20, which may be forwarded, at 544, to sensor system 8. This message may indicate that the computer 20 and/or sensor system 8 should enter a blind mode, so that the sensor data from the sensor system 8 should not be accessible and/or viewable by a user coupled to the sensor system 8.

At 546, the computer 20 and/or sensor system 8 may enter a blind mode, so that access to, and/or viewing of, any sensor data generated by sensor system 8 is inhibited at computer 20 and/or sensor system 8. For example, sensor data may be generated by sensor system 8 and/or forwarded to computer 20 and analyte processor 490 in a way that prevents the user coupled to, or wearing, the sensor system 8 from viewing and/or accessing the sensor data. However, this sensor data may be viewed by a clinician, doctor, and the like by accessing analyte processor 490. This blind mode allows a clinician, doctor, and the like to receive the data at analyte processor 490, generate a report, and discuss the results with the user wearing sensor system 8.

In some implementations, the computer 20 and/or sensor system 8 may provide an indication that they are in blind mode. For example, the sensor system 8 may present on a user interface and/or a display a message (e.g., "Blind") to indicate that the device is in a blind mode. Computer 20 may also present on user interface a message (e.g., "Blind") to indicate that the computer 20 is in a blind mode.

At 548, sensor system 8 may send sensor data to computer 20 via a wired link and/or a wireless link. The computer 20 may then forward the sensor data to analyte processor 490 for processing as disclosed herein. Moreover, the data pass through computer 20, so that data is not stored persistently at computer 20.

The computer 20 and/or sensor system 8 may remain in the blind mode (no at 550 and 552), until computer 20 and/or sensor system 8 receive another message, such as a command causing an un-blind of computer 20 and/or sensor system 8 (yes at 550 and 554). When the un-blind is received, computer 20 and/or sensor system 8 may configure operation so that a user coupled to, or wearing, sensor system 8 can access and/or view the sensor data at computer 20 and/or sensor system 8.

Figure 6:
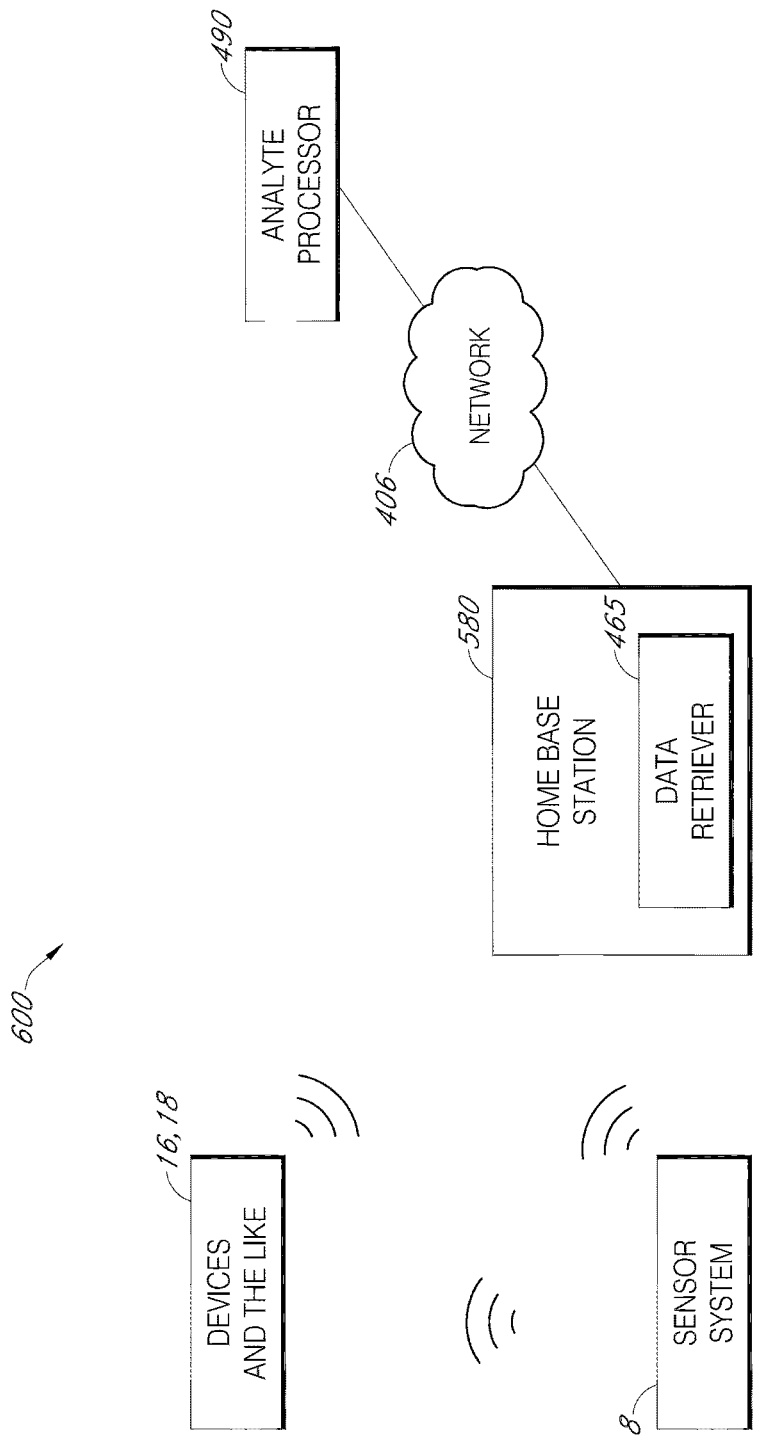
FIG. 6 depicts an example implementation of a system including a home base station, in accordance with some exemplary implementations.

FIG. 6 depicts an example implementation of a system 600 including a home base station 580. The home base station 580 may comprise at least one processor, at least one memory, and interfaces, such as wired and/or wireless interfaces, to the devices, such as devices 16, 18, and the like, and/or sensor system 8. The home base station 580 may also include data retriever 465, which may fetch data from sensor system 8 and forward the data through network 406 to analyte processor 490. In some implementations, the network may include a third party network. For example, the network 406 may include a wireless service provider network and/or may include network nodes and/or storage provided by an entity separate from analyte processor 490. For example, a service provider may provide home base station 560 and, in this example, the service provider may route (and/or store) the sensor data to analyte processor 490 via one or more network nodes of the service provider.

To illustrate by way of an example, home base station 580 may be a multi-mode communications device, such as a wireless access point, a home evolved Node B base station, a WiFi access point, and the like. As such, the home base station may include a plurality of radio interfaces, such as cellular interfaces, wireless local area network interfaces (e.g., WiFi), Bluetooth, Bluetooth Low-Energy, near field communications (NFC), ANT, and the like to enable communications with at least one of the sensor system, the devices, network 406, and the like. The home base station may also include a plurality of wired interfaces, such as a universal serial bus, Ethernet, and the like to enable communications with at least one of the sensor system, the devices, network 406, and the like. In this example, sensor system 8 and/or the device 16, 18, and the like, may couple via a wired or a wireless link to home base station 580 including data retriever 465, which forwards any received data to analyte processor 490 via network 406 (e.g., via a wireless network a wired network, the Internet, a cellular network, or a combination thereof).

In some implementations, home base station 580 may serve as a so-called docking station where the user may charge sensor system 8 and/or devices 16, 18, and the like.

In some implementations, the home base station 580 and the sensor system 8 (and/or devices 16, 18, and the like) are preconfigured, so that when the sensor system 8 and/or devices 16, 18, and the like couple to home base station 580, home base station 580 recognizes the sensor system/devices and/or a user thereof. For example, a health care provider may register sensor system 8 and home base station 580 with a specific user, and the registration may include an identifier and a key, such as a private key. This association may be stored at one or more of sensor system 8, home base station 580, and/or analyte processor 490. Moreover, this association may be configured and controlled by the analyte processor 490. In this example, when the paired sensor system 8 and home base station 580 couple, they automatically authenticate with an authenticator at a node, such as analyte processor 490 using the given key and/or identifier. And, analyte processor 490 automatically recognizes and recognizes the user registered with the sensor system 8 and home base station 580. When one or more host-users access the same home base station, analyte processor 490 may recognize each of the host-users based on other metadata, such as serial numbers associated with a sensor system 8, receiver 16, and/or any other information that can be used to distinguish between host-users. As such, the analyte processor 490 may automatically proceed with software installation, software updates, and the like as described herein with respect to 500, 598, 599, and the like. Moreover, the user coupled to, or wearing, sensor system 8 is required to do little, if anything, in order to upload data to analyte retriever 490 via home base station 580. For example, the user may just be within the wireless range of home base station 560 and/or establish a wired connection by, for example, docketing to home base station 580, and the data retriever 465 obtains sensor data and provides the data to analyte processor 490.

Analyte data processing system 400 may be implemented in a variety of configurations including stand-alone, distributed, and/or cloud-based frameworks. However, the following description relates to an implementation of system 400 in a cloud-based framework, such as a software-as-a-service (SaaS) arrangement in which the analyte processor 490 is hosted on computing hardware, such as servers and data repositories maintained remotely from an entity's location (e.g., remote from a host, a health service provider, and like end-user) and accessed over network 406 by authorized users via a user interface, such as user interfaces 410A-D, and/or a data retriever 465.

Figure 4B:
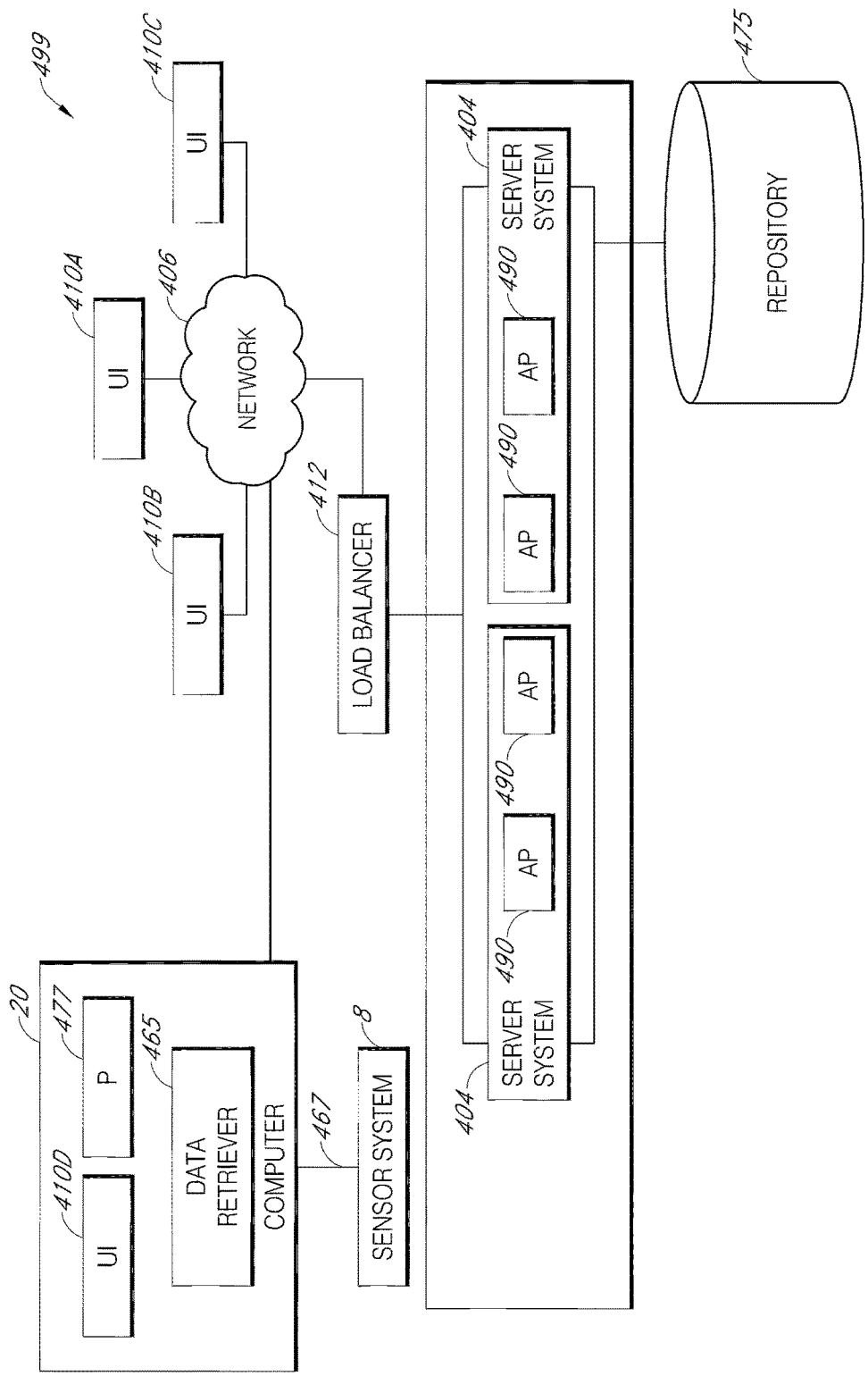

FIG. 4B depicts a system 499 which is similar to system 400, but system 499 is implemented as a SaaS-based system including a plurality of servers 404, each of which may be virtualized to provide one or more analyte processors 490. Moreover, each of the virtualized analyte processors 490 may serve a different tenant, such as an end-user, a clinic, a host wearing a sensor, and the like. To make more efficient use of computing resources of a software-as-a-service (SaaS) provider and to provide important performance redundancies and/or reliability, it may, in some implementations consistent with FIG. 4B, be advantageous to host multiple tenants (e.g., hosts, users, clinics, etc. at user interfaces 410A-D and/or data retriever 465) on a single system 400 and/or 499 that includes multiple servers and that maintains data for all of the multiple tenants in a secure manner at repository 475 while also providing customized solutions that are tailored to each tenant.

Figure 4C:
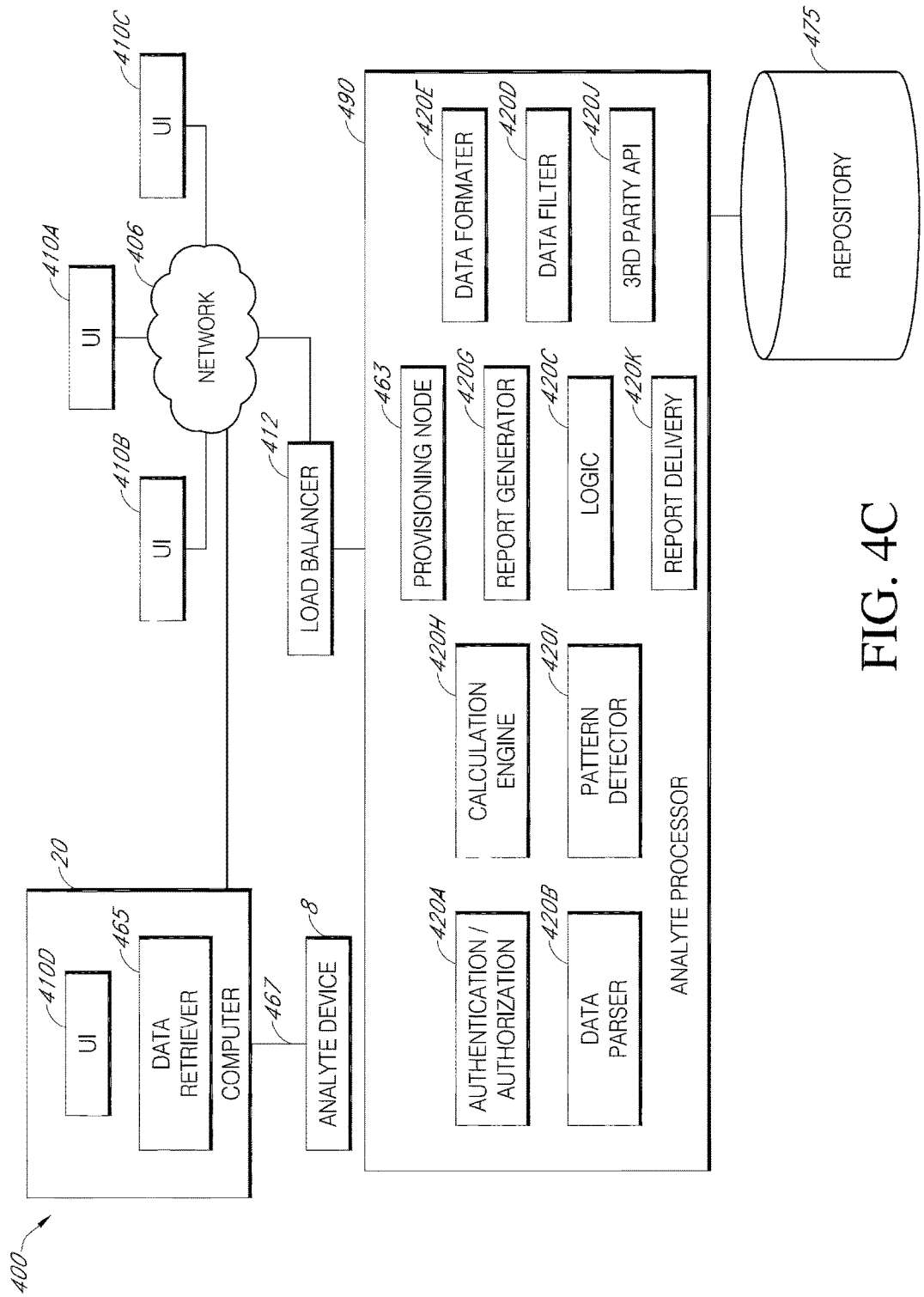

FIG. 4C depicts another implementation of the system 400 depicted at FIG. 4A. However, FIG. 4C depicts additional features at analyte processor 490. Referring to FIG. 4C, the analyte processor 490 may check data downloaded by the data retriever 465 for transmission-related errors, data formatting, device-related error codes, validity of the data, duplicate data points, and/or other aspects of the data. Moreover, if out-of-range data points or device errors are found, analyte processor may identify those data points by, for example, flagging those data points, subsequently correcting the identified data points programmatically or by a system administrator, and storing the corrected data points. Moreover, the analyte processor may be configured by a user, such as a clinician, doctor, and the like, to perform additional data processing steps, such as correcting time of day, correcting the date, and analyzing data by specific cohorts, groups, and relationships (e.g., demographics, such as age, city, state, gender, ethnicity, Type I diabetes, Type II diabetes, age of diabetes diagnosis, lab results, prescription drugs being used, self-reported conditions of the patient, diagnosed conditions of the patient, responses to questions posed to patient, and any other metadata representative of the host/patient). Once analyte processor performs initial data processing (e.g., checks, cleaning, and analysis), the processed data and/or the raw data provided by the data retriever may be stored at repository 475.

The processing at analyte processor 490 may also include associating metadata with the data received from the devices and/or sensors. Examples of metadata include patient information, keys used to encrypt the data, patient accelerometer, location data (e.g., location of patient or location of patient's clinic), time of day, date, type of device used to generate associated sensor data and the like. The patient information can include the patient's age, weight, sex, home address and/or any past health-related information, such as whether the patient has been diagnosed as a Type 1 or Type 2 diabetic, high-blood pressure, or as having any other health condition. The processing may also include analysis, such as determining one or more descriptive measurements and/or generating reports based on received information and descriptive measurements. These descriptive measurements may include statistics (e.g., median, inner and outer quartile ranges, mean, sum, n, standard deviation, and coefficients of variation).

In some exemplary implementations, the analyte processor 490 may process the received data by performing one or more of the following: associating metadata with the data received from the devices, sensors, source system, and/or data retriever; determining one or more descriptive measurements, such as statistics (e.g., median, inner and outer quartile ranges, mean, sum, n, and standard deviation); generating reports including descriptive measurements; validating and verifying the integrity of the received data from the devices, sensors, source system, and/or data retriever;

processing received data based on metadata (e.g., to select certain patients, devices, conditions, diabetic type, and the like), and/or correlating received data from the devices, sensors, source system, and/or data retriever, so that the data can be compared and combined for processing including analysis.

Moreover, the results of any processing performed by analyte processor 490 may be used to generate one or more reports, such as graphs, bar graphs, static charts, charts, and the like. Furthermore, the reports and other outputs generated by system 400 may be provided via one or more delivery mechanisms, such as report delivery module 420K (e.g., as email, secure email, print, text, presentations for display at a user interface, such as at user interface 410A-D hosted at a tablet or other processor), machine-to-machine communications (e.g., via third party interface 420J), and any other communication mechanism.

In some exemplary implementations, the reports may be customized dynamically for use by an entity, such as a host, an end-user, a clinician, a healthcare provider, device manufacturer and the like. Furthermore, the reports may be customized based on the types and/or quantity of sensors and systems providing data to system 400 and the types of metadata available to system 400. This customization may be performed by a user, by system 400 programmatically, or a combination of both.

In some exemplary implementations, one or more of the user interfaces 410A-D may be implemented on a processor, such as computer 20 or other processor, serving a kiosk at a health care provider, clinic, and the like. For example, a user, such as a host (also referred to as a patient), may enter a health care facility and access the kiosk in order to couple and to provide sensor data and/or metadata to system 400. In this example, the user may provide sensor data and/or metadata to system 400 and then view at one or more of user interfaces 410A-D one or more reports including information representative of the sensor data and/or metadata provided to system 400 including statistical measures of the data. Although the previous example using the kiosk, the kiosk may also be used by a health care provider or administrative staff as well.

Although the previous example refers to computer 20 including a user interface and a data retriever to provide a kiosk, the user interface may be located in other devices, such as smart phones, tablet computers, display devices, and other like processors. Moreover, the computer 20 may be located at locations other than a kiosk. For example, computer 20 may be located at a host's home and include a data retriever 465 to retrieve data from a sensor associated with the host, so that the data retriever 465 can format and provide the sensor data to analyte processor 490. The user interface and data retriever may also be configured at a workstation of a health care provider or clinician.

Analyte processor 490 may include, in some exemplary implementations, an authenticator/authorizer 420A for authorizing access to analyte processor 490, a data parser 420B for parsing requests sent to analyte processor 490, a calculation engine 420H for receiving data from sensors and processing the received data into counts for use with histograms, logic 420C, a data filter 420D, a data formatter 420E, a report generator 420G, a pattern detector 420I, a report delivery module 420K for delivering reports in a format for the destination, and a third party access application programming 420J interface to allow other systems and device to access and interact with analyte processor 490.

Analyte processor 490 may receive a request from a user interface, such as user interfaces 410A-D, to perform an action (e.g., provide data, store data, analyze/process data, request a report, and the like). Before analyte processor 490 services the request, the analyte processor 490 may process the request to determine whether the request is authorized and authenticated. For example, authenticator and authorizer 420A may determine whether the sender of the request is authorized by requiring a user to provide a security credential (e.g., a user identifier, a password, a stored security token, and/or a verification identifier provided by text message, phone, or email) at a user interface presented on a computer. If authorized, authenticator and authorizer 420A may authenticate the sender of the request to check whether a security credential associated with sender of the request indicates that the sender (e.g., a user at user interface 410A) is indeed permitted to access a specific resource at system 400 in order to perform the action, such as store (or upload) data at repository 475, perform analyze/process data, request report generation, and the like.

To further illustrate, the data retriever 465 associated with a sensor system 8 and a computer 20 may be authorized and authenticated by authenticator and authorizer 420A to access analyte processor 490 in order to write data to a buffer or other storage mechanism, such as repository 475. On the other hand, an entity, such as a user, at user interface 410A may be authorized and then authenticated by authenticator and authorizer 420A to access analyte processor 490, but only permitted to access certain information. In this second example, the user at user interface 410A may be authorized and authenticated to access repository 475 to view certain information corresponding to the user's own glucose data and access reports generated for the glucose data, but the user will not be authorized and authenticated to access another user's data and/or reports. Another example may be the case when a user associated with a clinic, a hospital, and/or a research group requests access to all data associated with their patients. In this example, the user may be granted access to their patients but not other patients. Yet another example may be the case when a user associated with a clinic, a hospital, and/or a research group requests access to all data associated with patients using a certain device, such as a specific type analyte sensor. In this example, the user may be granted access to data specific to the type of analyte sensor but not other sensors (and personal identifiable information (PII) may be removed or made anonymous).

Once authorized and/or authenticated, the request received at analyte processor 490 may then be parsed by data parser 420B to separate any data, such as sensor data, metadata, and the like, from the request. In some implementations, data parser 420B may perform check data formatting, device-related error codes, validity of the data, duplicate data points, and/or other aspects of the data. Moreover, the data parser 420B may associate additional metadata with the separated data. The metadata may include any of the meta data described herein, including an owner of the data, a key to track the data, an encryption key unique to each user, time of day, date information, one or more locations where the data is (or will be stored), and the like. In some exemplary implementations, the data parsing 420 may provide data to the calculation engine 420H for formatting the data into counts and histograms as described further below.

In some exemplary implementations, the request (or the parsed data therein) may be processed by calculation engine 420H. The calculation engine 420H preprocesses the data received from devices, sensors, and the like to form "counts." The counts represent a measured value, such as an analyte value measured by a sensor, a glucose value measured by a sensor, a continuous glucose value measured by a sensor, and/or other diabetes related information, such as carbohydrates consumed, temperature, physical activity level, and the like, and how often that measured value occurred.

Figure 4D:
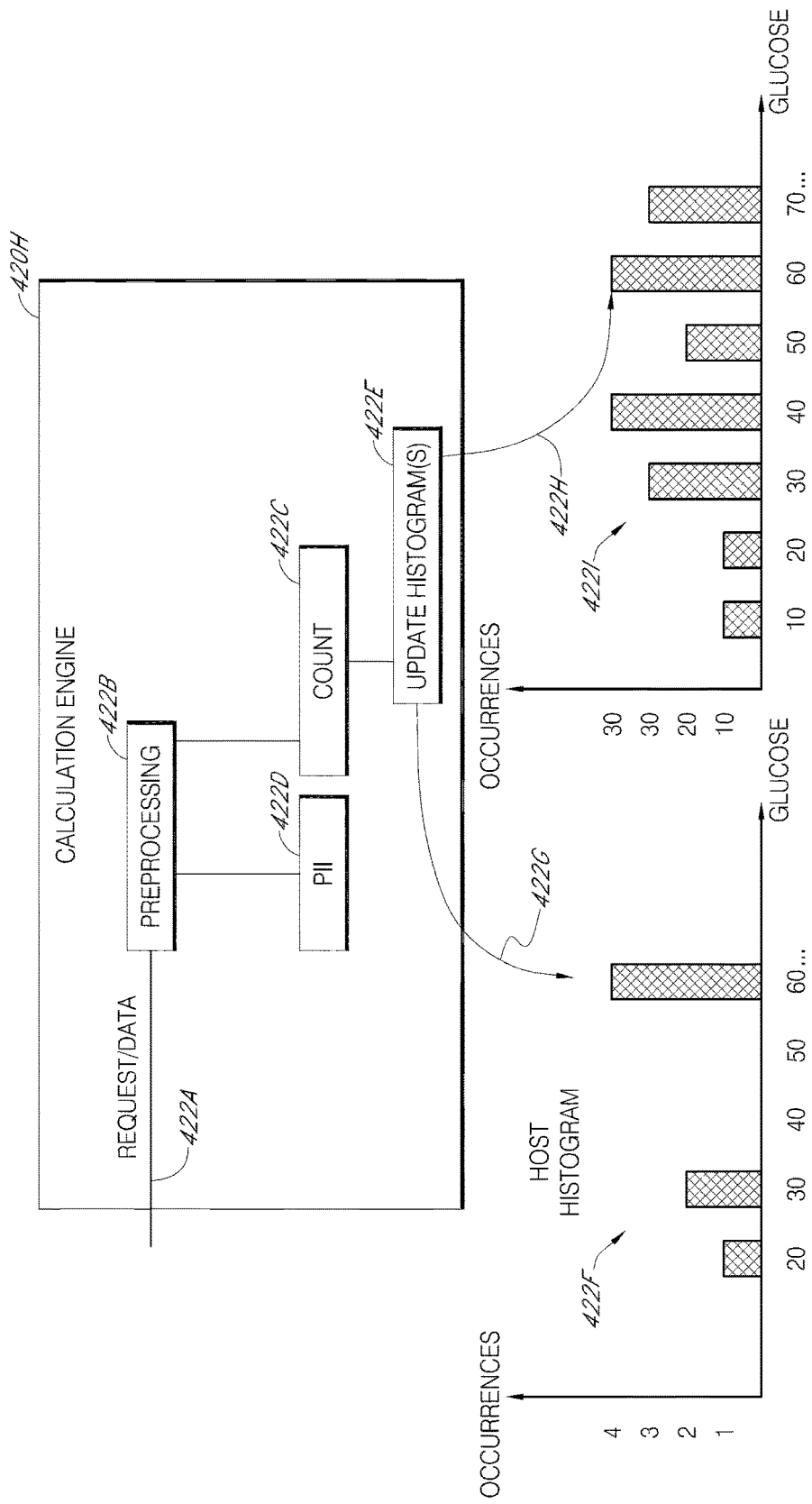
FIG. 4D depicts a block diagram of a calculation engine configured to generate counts representative of analyte levels in a host in accordance with some exemplary implementations.

FIG. 4D depicts an example implementation of the calculation engine 420H. When a request 422A is received at the calculation engine 420H, the calculation engine 420H may preprocess 422B the request to extract data, such as sensor data, and thus form a count. The count may represent a numerical value representative of sensor data provided by, for example, data retriever 465, computer 20, sensor system 8, and/or any other source of data and how often it occurred. For example, the count may represent a glucose value measured by a continuous glucose sensor, such as continuous analyte sensor 10, and how often it occurred over a certain period of time.

The calculation engine 420H may also preprocess 422B the request 422A to provide and/or determine other metadata, such as to determine personal identifiable information (PII) 422D associated with the request 422A, time of day/date, and the like, although in some implementations the calculation engine may receive the request without PII information. The PII may include a serial number of the sensor system 8 and any other information that may identify the host associated with sensor system 8. In some exemplary implementations, the PII may be stored in repository 475 in an encrypted form to enhance the privacy of the PII. Furthermore, the PII may be encrypted with an encryption technique and/or key that is different from other information stored at repository 475. For example, analyte processor 490 may store at repository 475 data from a plurality of users, such as hosts, patients, and the like. To maintain privacy, each user's data may be encrypted with a separate key. Moreover, PII information may be encrypted with yet another key to further enhance the privacy of the user.

The calculation engine 420H may then use the count 422C to perform additional processing. The additional processing may include storing the count in repository 475, which may include one or more databases to store the counts. Moreover, the count may be stored with metadata, such as time of day/date information, the original request 422A, and the like. Furthermore, the count may be encrypted, as noted, before storage in repository 475, and, in some exemplary implementations, the count and/or metadata may be encrypted with an encryption technique and/or key that is different from the PII.

Although some of the examples described herein refer to databases, the databases may also be implemented as any type of data store, such as relational databases, non-relational databases, file systems, and the like.

The calculation engine 420H may also use the count to update one or more histograms 422E. For example, rather than keep track of and process a host's glucose levels over a certain period of time using raw sensor data values, the calculation engine 420H may convert the data values into counts. The counts may be added to a histogram 422F for a given host. In the example of FIG. 4D, the histogram 422F includes an x-axis of glucose concentration values and a y-axis of the number of occurrences for each glucose concentration value. In this example, if the count 422C for a host is 60, the calculation engine 420H updates 422G the bin associated with the value 60. The histogram 422F may be associated with a given patient/host to represent the glucose levels of the host.

In some exemplary implementations, the histogram 422F may also be associated with a given time during the day (also referred to as an epoch). For example, histogram 422F may represent a time, such as 1 PM to 1:30 PM, and, in this example, calculation engine 420H may generate other histograms for other times.

In some exemplary implementations, the calculation engine 420H may generate a plurality of histograms for a given host for given time periods. For example, 48 histograms corresponding to 30-minute epochs over a 24 hour period may be generated, so that each time a count is received, the count is added to one of the 48 histograms based on a time associated with the count and a corresponding histogram. In this example, a count representative of a blood glucose measurement made at 12:30 AM would update a histogram designated to cover measurements made during that epoch, while another count with a time of day at 1:30 AM would update another histogram assigned to represent the 1:30 AM epoch. Moreover, these 48 histograms may be stored in a database in a data structure to facilitate access. For example, each of the 48 histograms may be stored as rows in a database. Moreover, calculation engine may determine, based on the one or more histograms, statistics using set theory as described further below.

Although the previous example utilizes a 30-minute interval as an epoch, other intervals of time, such as 15 minutes, and the like, may be used as well.

In some exemplary implementations, the calculation engine 420H may also update other histograms representative of aggregate count information. For example, the count 422C may be used to update histograms 422E representative of so-called "cohorts" of the host used to generate histogram 422F. The term "cohorts" refers to hosts that can be grouped, and this grouping may be based on one or more factors, such as a demographic, a health condition, an age, a geographic location (e.g., country, state or zip code), and the like. In the example of FIG. 4D, the histogram 422G is updated 422H with the same count value as histogram 422F, but the histogram 422G represents cohorts associated with, for example, all of the other patients in a clinic where the host is being treated. As such, histogram 422G may provide insight into the host and the host's cohorts at the clinic.

Moreover, the calculation engine 420H may also update other histograms used to pre-calculate statistics associated with the host or cohorts. For example, the calculation engine may update histograms (which are associated with a certain patient) and update other histograms (which may be for other patients, such as cohorts selected based on metadata, such as a zip code, an age, a gender, and the like). In addition, the calculation engine 420H may also form other histograms based on statistics, such as a union, an intersection, a set difference, and the like. For example, calculation engine 420H may use set theory to determine the union of histograms. The union represents the set of all objects that are in a first histogram A, a second histogram B, or a combination of both (denoted A ∩ B). The calculation engine 420H may also determine intersections (e.g., the set of all objects that are only in first histogram A and the second histogram B, denoted A U B), and may determine the set difference (e.g., the set of all members of the first histogram A that are not in second histogram B, denoted A\B).

In some implementations, the calculation engine uses the histograms and set theory operations to determine aggregate statistical information and to form a so-called aggregate histogram. For example, a report may be generated to include an aggregate histogram for all patients in a geographic region, such as the United States. In this example, the calculation engine may identify existing histogram groups that provide the smallest number of histograms to cover the geographic region of interest. Specifically, the histograms of all patients (or clients) that are in the United States may be merged using set theory to form a virtual histogram of the United States for a given time frame, such as the past 30 days. In addition, this operation may, in some implementations, be performed very rapidly, when compared to performing such operations on raw sensor data. In some implementations, the repository may store a plurality of histograms (e.g., histograms may be organized based on patient, clinic, zip code, etc.) which can be readily processed using set theory to form the aggregate histogram or determine statistics for the aggregate histogram. Moreover, in some implementations, an aggregate histogram may be configured for storage at the repository, in which case the calculation would update the aggregate histogram with counts rather than generate it using set theory. Although the previous example refers to the aggregate histogram generated based on geographic location, the aggregate histogram may be generated on other metadata described herein as well (e.g., demographics, age, zip code, type of diabetes, age of diagnosis, and the like).

In some implementations, the calculation engine 420H may have to update, as noted, a plurality of histograms. When this is the case, the calculation engine 420H may update the histograms in a distributed manner based on eventual consistency.

Although the description with respect to the calculation engine 420H refers to a histogram, the histogram, as used herein, refers to a data structure that includes one or more values (e.g., values) associated with one or more time intervals. For example, the histogram may represent one or more values, such as frequency of occurrence, associated with bins corresponding to one or more time intervals. Moreover, this data structure may be stored at a database, so that it is readily accessed with a read, such as in a row of a database (or, for example, in a column if a column database is used).

In some exemplary implementations, repository 475 stores the histograms including counts in a database. For example, repository 475 may store data for a patient that covers a time frame, such as 1 day, 2 days 7 days, 30 days, or more. In this example, the days may be subdivided into epochs, each of which has a corresponding histogram stored in repository 475. Moreover, each histogram may be stored as a row (or column) in a database at repository 475 to facilitate fast data access.

Referring again to FIG. 4C, logic 420C may also process requests to perform an action (e.g., store, retrieve, process, analyze, report data, and the like) at analyte processor 490. For example, logic 420C may control the actions of the analyte processor 490 when processing a request to store data at repository 475. In this example, the request may, under control of logic 420C, be parsed at data parser 420B, converted into a count at calculation engine 420H, added to histogram 422F-422G, and then forwarded to repository 475 for storage. Moreover, this process may occur serially and/or asynchronously (e.g., the data parser may extract data and provide data for asynchronous updating of counters associated with histograms, and the subsequent data store at the repository may occur asynchronously or substantially simultaneously).

Logic 420C may also determine one or more descriptive measurements, such as statistics (e.g., a median, inner and outer quartile ranges, a mean, a sum, a standard deviation, and the like) based on counts, histograms, and/or received sensor data. The logic 420C may provide these descriptive measurements to the report generator 420G to enable report generation (e.g., for presentation at a user interfaces 410A-D). For example, the mean may be determined by summing the product of the count and the bin value and then dividing that sum by the sum of the counts. Referring again to FIG. 4D at histogram 422F, the mean is 46 (20*1+30*2+60*4)/(1+2+6).

The pattern detector 420I may perform pattern detection on data, such as sensor data representative of blood glucose data, analytes, and other data as well (e.g., insulin pump data, carbohydrate consumption data, and the like) processed by analyte processor 490 and stored at repository 475. Moreover, the pattern detector 420I may detect patterns retrospectively for a predetermined time period defined by system 400 and/or a user.

In some exemplary implementations, the pattern detector 420I may receive input data from the repository 475, and the input data may include sensor data representative of glucose concentration data, analytes, and other data as well (e.g., insulin pump data, carbohydrate consumption data, histograms and/or counts, data from a continuous glucose monitor (CGM data), time of day, amount of carbohydrates, other food related information, exercise, awake/sleep timer intervals, medications ingested, and the like). Moreover, the input data may comprise historical data obtained over a time frame, such as 8 hours, 1 day, 2 days, 7 days, 30 days, and/or any other time period. For example, the input data may comprise counts representative of monitored analyte detection levels (e.g., glucose concentration levels) received and stored at system 400 over a period covering a four-week time frame.

The pattern detector 420I may analyze the input data for patterns. For example, patterns can be recognized based on one or more predefined rules (also referred to as criteria or triggers). Furthermore, the one or more predefined rules may be variable and adjustable based user input. For example, some types of patterns and rules defining patterns can be selected, turned off and on, and/or modified by a user, a user's physician, or a user's guardian, although system 400 may select, adjust, and/or otherwise modify rules programmatically as well.

Some examples of the types of relationships in the input data that can be considered a pattern are one or more of the following: a glucose level that exceeds a target glucose range (which may be defined by a user, health care provider, system 400, or a combination thereof); a glucose level that is below a target glucose range; a rapid change in glucose level from a low to a high (or vice versa); times of day when a low, a high, an at range, or rapid glucose level event occurs; and/or days when a low, a high, an at range, or a rapid glucose level event occurs.

Additional examples of the types of relationships in the input data that can be considered a pattern include hypoglycemic events by time of day. As an example, a pattern may be identified in situations where the user has low glucose concentrations around the same time in the day. Another type of pattern, which may be identified, is a "rebound high" situation. For example, a rebound high may be defined as a situation where a user overcorrects a hypoglycemic event by overly increasing glucose intake, thereby going into a hyperglycemic event. These events may be detected based on one or more predefined rules. Patterns that may be detected include a hyperglycemic pattern, a hypoglycemic pattern, patterns associated with a time of day or week, a weighted scoring for different patterns based on frequency, a sequence, and a severity. Patterns may also be based on a custom sensitivity of a user, a transition from a hypoglycemic to hyperglycemic pattern, an amount of time spent in a severe event, and a combination of glucose change and time information. Detected patterns may also be patterns of high variability of glucose data. Further, a pattern may be based on a combination of previous pattern data and a currently detected situation, whereby the combined information generates a predictive alert.

The pattern detector 420I may detect the pattern and generate an output, which may be provided to report generator 420G for reporting. Moreover, the report may include a retrospective analysis of the input data and any patterns determined by pattern detector 420I. Although the previous example describes an approach for detecting patterns in data, other approaches may be used as well.

The data filter 420D may be used to check whether an output generated by analyte processor 490, such as a response for certain types of data, a report, and the like, does not violate a data rule. For example, the data filter 420D may include a data rule to check whether a response includes data, such as PII, to a destination which is not authorized or allowed to receive the response (e.g., based upon authorization and authentication and the corresponding role of the user making the request).

The data formatter 420E may format data for delivery based on the type of destination. For example, the data formatter 420E may format a report based on whether it is being sent to a printer, a user interface, a secure email, another processor, and the like.

The report generator 420G may generate one or more reports. The reports may provide descriptive information, such as statistical information, representative of the sensor data received at analyte processor 490. Moreover, the report may provide a retrospective analysis of the sensor data stored at repository 475. For example, the report may provide statistical information based on sensor data (and/or corresponding histograms including counts) over a time frame, such as 8 hours, 1 day, 2 days, 7 days, 30 days, and any other time frame. Moreover, the report may allow a user, such as a patient, a host, or a clinician, to view the report and identify trends and other health related issues.

Figure 7:
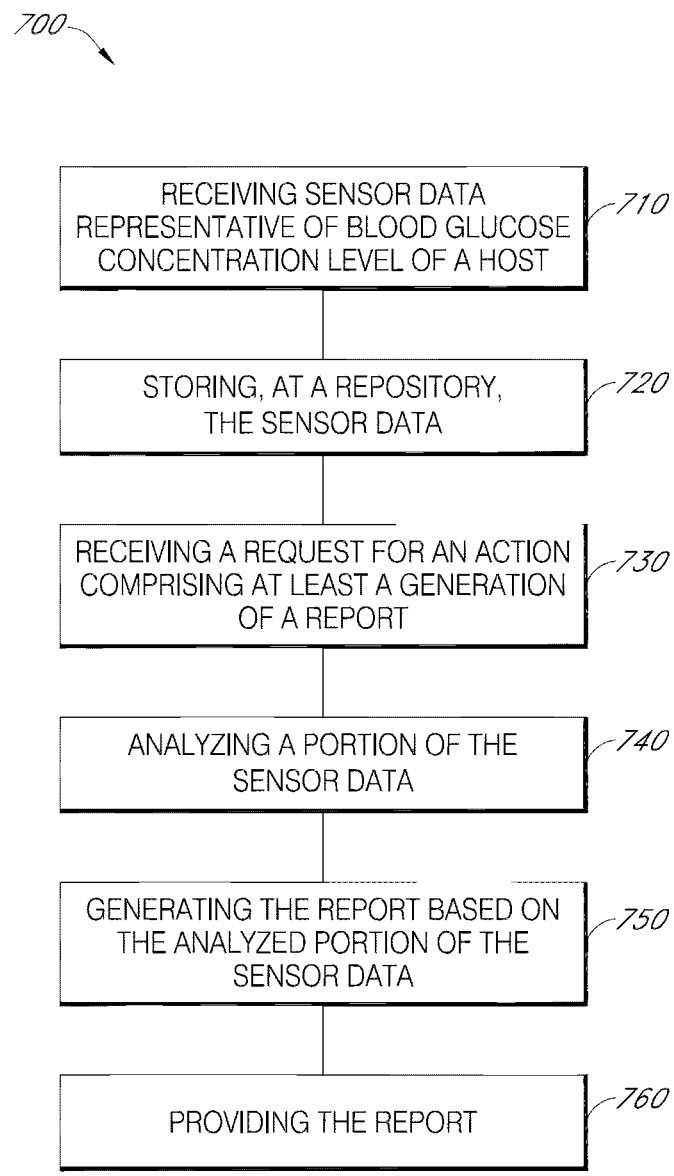
FIG. 7 depicts an example of a process for processing analyte data in accordance with some exemplary implementations.

FIG. 7 depicts an example of a process 700 for processing analyte data, in accordance with some exemplary implementations. The description of process 700 may also refer to FIGS. 1 and 4A-D.

At 710, sensor data representative of an analyte measured in a host may be received, in accordance with some exemplary implementations. For example, analyte processor 490 may receive sensor data, such as values representative of blood glucose levels, from one or more devices, such as display devices 14, 16, 18, 20, sensor system 8, data retriever 465, user interfaces 410A-D, and the like, using a data retrieval process described herein. The analyte processor 490 may also receive (and/or determine) metadata associated with the analyte data, such as patient information, time of day associated with the measurement of the analyte data, and the like. Analyte processor 490 may process the received sensor data and/or metadata using one or more aspects of analyte processor 490 (e.g., authentication authorization 420, data parser 430B, calculation engine 420H, pattern detector 420I, report generator 420G, and the like as disclosed herein) and store the received sensor data and/or metadata in repository 475. Although the description of process 700 refers to sensor data, analyte processor 490 may process other types of data as well. At 720, sensor data and/or metadata received at analyte processor 490 may be stored at repository 475 based on histograms and counts associated with the received sensor data and/or metadata, in accordance with some exemplary implementations. For example, the sensor data and/or metadata received at 710 may be processed by calculation engine 420H to form counts, as noted above with respect to FIG. 4D. In addition, the counts are then added to corresponding histograms (which may be stored at repository 475) based on metadata, such as a time of day associated with when measurement and the identity of the patient. In some exemplary implementations, the counts may be added to other histograms associated with cohorts. The repository 475 may store received sensor data, metadata, histograms, and/or counts for one or more patients (also referred to as hosts) for a time frame of 8 hours, 1 day, 2 days, 7 days, 30 days, or more to enable system 400 to analyze the stored data and generate the reports disclosed herein.

At 730, the analyte processor 490 may receive a request to perform an action in accordance with some exemplary implementations. For example, analyte processor 490 may receive the request from a system, a processor, and/or a user interface, such as user interface 410A. The action may correspond to a request to generate a report for a certain patient, although other actions may be requested as well. The request may also indicate a time frame for the report, although the time frame may be determined programmatically by system 400 as well. The request may indicate other aspects of the request, such as types of modules to be included in the report. In some exemplary implementations, the request may undergo additional processing, such as authorization, authentication, parsing, and the like at analyte processor 490.

Moreover, the request may also correspond to other actions at analyte processor 490. Examples of actions include storing sensor data, metadata, and any other type of data at repository 475, retrieving sensor data, metadata, and any other type of data at repository 475, configuring reports and/or modules, customizing aspects of system 400 (e.g., adding devices, customizing reports, target glucose ranges, time frames for reports, and the like).

At 740, analyte processor 490 and/or logic 420 may evaluate the time frame of the report, the patient's identity, and other metadata associated with the patient (e.g., number of devices, types of devices, and the like) and analyze a portion of the sensor data associated with the time frame. To illustrate further, logic 420 may determine that the time frame of a report is the past 30 days, the patient's identity 605A, and that the patient is associated with a single type of continuous blood glucose monitoring device. In this example, logic 420C may determine descriptive measurements (e.g., one or more statistics) for the past 30 days for the patient based on the data stored at repository 475 and/or request pattern generator 420I to detect patterns for the patient's data stored at repository 475 in the last 30 days. In some exemplary implementations, the time frame of the report and the corresponding data evaluated for the report is selected by a user (e.g., a patient, a clinician, and the like) or programmatically by system 400.

At 750, logic 420 may initiate report generation at report generator 420G based on the analysis performed at 740. For example, logic 420 may evaluate the time frame of the report, the patient's identity, and other metadata associated with the patient (e.g., number of devices, types of devices, and the like), and determine the type of modules to include in the report and the configuration of those modules. To illustrate further, logic 420 may determine that the time frame of the report is the past 30 days, the patient's identity, and that the patient is associated with a single continuous glucose monitoring device. In this example, logic 420C may determine modules customized to present an analysis, such as statistics and patterns, for continuous blood glucose monitoring data. Although the previous example refers to the generated report as a graphical report, the report may be text based as well or may be generated as a machine-to-machine data exchange.

At 760, the generated report may be provided to, for example, a user interface, such as user interface 410A-D, another machine, and the like.

Referring again to FIGS. 4A-C, the system 400 may store, in some exemplary implementations, health data separately from personally identifiable information, which is encrypted. For example, system 400 may include a security layer below the logic layer so that encryption occurs when data is stored to repository 475. In some exemplary implementations, the encryption is based on multiple factors, such as the host, the storage location (e.g., row-column information), and the like. For example, an encryption algorithm, such as the advanced encryption algorithm and the like may be implemented. In some implementations, the encryption keys may be split and stored on separate portions of system 400 (e.g., on analyte processor 495, servers for the databases, and the like) with separate user credentials for authentication.

In some exemplary implementations, the repository 475 is distributed. For example, the repository 475 may comprise a plurality of persistent storage devices, which are distributed. Moreover, the persistent storage devices may include one or more of relational databases, non-relational document stores, non-relation key-value data stores, hierarchical file system-like stores (also referred to as data stores), and the like. Furthermore, the repository 475 may be replicated so that the storage devices are geographically dispersed.

Various implementations of the subject matter described herein may be realized in digital electronic circuitry, integrated circuitry, specially designed ASICs (application specific integrated circuits), computer hardware, firmware, software, and/or combinations thereof. The circuitry may be affixed to a printed circuit board (PCB), or the like, and may take a variety of forms, as noted. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications, or code) include machine instructions for a programmable processor, and may be implemented in a high-level procedural and/or object-oriented programming language, and/or in assembly/machine language. As used herein, the term "machine-readable medium" refers to any non-transitory computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

Although a few variations have been described in detail above, other modifications are possible. For example, while the descriptions of specific implementations of the current subject matter discuss analytic applications, the current subject matter is applicable to other types of software and data services access as well. Moreover, although the above description refers to specific products, other products may be used as well. In addition, the logic flows depicted in the accompanying figures and described herein do not require the particular order shown, or sequential order, to achieve desirable results. As used herein, the term "based on" also refers to "based on at least." Other implementations may be within the scope of the following claims.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method comprising:
    inhibiting access at a data receiver device to analyte sensor data indicative of measured analyte concentration levels in a host, when a command is received to place in a blind mode one or more devices including a sensor device configured to measure the analyte concentration levels in the host and the data receiver device configured to receive data from the sensor device;
    forwarding the analyte sensor data to an analyte processing system;
    determining whether an unblinded command is received from the analyte processing system and continuing to operate in the blind mode upon determining that the unblinded command has not been received from the analyte processing system;
    deriving a numerical representation of the analyte concentration values using the analyte sensor data;
    accessing the forwarded analyte sensor data from the analyte processing system by an authorized user; and
    wherein the inhibiting access to the analyte sensor data prevents the sensor device and the data receiver device from displaying the analyte sensor data stored in memory therein, and wherein the accessing includes at least displaying the numerical representation of the forwarded analyte sensor data to the authorized user.

2. The method of claim 1, wherein the data receiver device couples to the sensor device via a first encrypted connection and further couples through a second encrypted connection to the analyte processing system.

3. The method of claim 1, further comprising:
receiving, from the analyte processing system, the command to place in the blind mode and the sensor device.

4. The method of claim 1, further comprising receiving the forwarded data by the analyte processing system from the data receiver device and deriving analyte concentration values using the forwarded data.

5. The method of claim 1, wherein the displaying comprising generating a report for the authorized user based on the forwarded analyte sensor data.

6. The method of claim 1, further comprising configuring the data receiver device or the sensor device for unblinded operation upon determining that the unblinded command has been received.

7. The method of claim 1, comprising providing notification at the receiver device about the blind mode and the unblind mode.

8. A data receiver device comprising:
at least one processor; and
at least one memory including code which when executed by the at least one processor provides operations comprising:
inhibiting at the data receiver device access to analyte sensor data indicative of measured analyte concentration levels in a host, when a command is received to place in a blind mode one or more devices including a sensor device configured to measure the analyte concentration levels in the host and the data receiver device configured to receive data from the sensor device: and
forwarding the analyte sensor data to an analyte processing system wherein the forwarded analyte sensor data is being accessed by an authorized user of the analyte processing system;
determining whether an unblinded command is received from the analyte processing system and continuing to operate in the blind mode upon determining that the unblinded command has not been received from the analyte processing system;
deriving a numerical representation of the analyte concentration values using the analyte sensor data; and
wherein the inhibiting access to the analyte sensor data prevents the sensor device and the data receiver device from displaying the analyte sensor data stored in memory therein, and wherein the analyte processing system facilitates display of the numerical representation of the forwarded analyte sensor data to the authorized user.

9. The data receiver device of claim 8, configured to couple to the sensor device via a first encrypted connection and is further configured to couple through a second encrypted connection to the analyte processing system.

10. The data receiver device of claim 8, further configured to receive, from the analyte processing system, the command for the blind mode, and wherein the sensor device receives the blind mode command from the analyte processing system or the data receiver device.

11. The data receiver device of claim 8, wherein the forwarded analyte sensor data is received by the analyte processing system to derive analyte concentration values.

12. The data receiver device of claim 8, wherein the display includes generation of a report for the authorized user based on the forwarded analyte sensor data.

13. The method of claim 8, further configured to operate in an unblinded mode or place the sensor device in an unblinded mode upon the determination that the unblinded command has been received.

14. The method of claim 8, is configured to provide notification to the host about the blinded and the unblinded mode.

* * * * *

UNITED STATES PATENT AND TRADEMARK OFFICE
CERTIFICATE OF CORRECTION

| | | |
|---|---|---|
| PATENT NO. | : 10,009,407 B2 | Page 1 of 1 |
| APPLICATION NO. | : 15/642729 | |
| DATED | : June 26, 2018 | |
| INVENTOR(S) | : Daniel N. Root et al. | |

It is certified that error appears in the above-identified patent and that said Letters Patent is hereby corrected as shown below:

On the Title Page

Column 1, (Notice) at Line 3, After "0 days." delete "days.".

In the Drawings

Sheet 6 of 14 (Reference Numeral 420E) (FIG. 4C) at Line 1, Change "FORMATER" to --FORMATTER--.

In the Specification

In Column 23 at Line 48, Change "heath-related" to --health-related--.

In Column 33 at Line 18, Change "Pll" to --PII--.

Signed and Sealed this
Second Day of October, 2018

Andrei Iancu
*Director of the United States Patent and Trademark Office*